United States Patent
Caiazza

(10) Patent No.: US 10,457,970 B2
(45) Date of Patent: Oct. 29, 2019

(54) EXPRESSION OF MODIFIED GLYCOPROTEINS AND GLYCOPEPTIDES

(71) Applicant: Conagen Inc., Bedford, MA (US)

(72) Inventor: Nicky C. Caiazza, Rancho Santa Fe, CA (US)

(73) Assignee: Conagen Inc., Bedford, MA (US)

(*) Notice: Subject to any disclaimer, the term of this patent is extended or adjusted under 35 U.S.C. 154(b) by 0 days.

(21) Appl. No.: 15/799,785

(22) Filed: Oct. 31, 2017

(65) Prior Publication Data

US 2018/0119193 A1 May 3, 2018

Related U.S. Application Data

(60) Provisional application No. 62/416,086, filed on Nov. 1, 2016.

(51) Int. Cl.

| | |
|---|---|
| *C07K 14/705* | (2006.01) |
| *C12N 1/00* | (2006.01) |
| *C12N 9/24* | (2006.01) |
| *C12N 15/79* | (2006.01) |
| *C12P 21/00* | (2006.01) |
| *C07K 16/32* | (2006.01) |
| *C12N 9/10* | (2006.01) |

(52) U.S. Cl.
CPC ............ *C12P 21/005* (2013.01); *C07K 16/32* (2013.01); *C12N 9/1051* (2013.01); *C12N 15/79* (2013.01); *C12Y 204/01258* (2013.01); *C07K 2317/14* (2013.01); *C07K 2317/41* (2013.01)

(58) Field of Classification Search
CPC ............................. C07K 14/705; C12N 15/79
See application file for complete search history.

(56) References Cited

U.S. PATENT DOCUMENTS

| | | | |
|---|---|---|---|
| 8,026,083 B2* | 9/2011 | Callewaert | C07K 14/00 435/69.1 |
| 8,409,825 B2 | 4/2013 | Chiba et al. | |
| 9,428,784 B2 | 8/2016 | Choi et al. | |
| 2004/0018590 A1 | 1/2004 | Gerngross et al. | |
| 2006/0253928 A1 | 11/2006 | Bakker et al. | |
| 2010/0227363 A1 | 9/2010 | Bosh et al. | |
| 2011/0118331 A1 | 5/2011 | Behr et al. | |
| 2011/0195480 A1 | 8/2011 | Bayne et al. | |
| 2013/0040897 A1 | 2/2013 | Aebi et al. | |
| 2013/0231255 A1 | 9/2013 | Collins et al. | |
| 2015/0132803 A1 | 5/2015 | Apt et al. | |

FOREIGN PATENT DOCUMENTS

| | | |
|---|---|---|
| WO | WO 2006/014685 A1 | 2/2006 |
| WO | WO 2007/006570 A2 | 1/2007 |
| WO | WO 2007/084922 A2 | 7/2007 |

OTHER PUBLICATIONS

International Search Report dated Jan. 19, 2018 regarding PCT/US2017/059304.

Nasab et al.: "A combined system for engineering glycosylation efficiency and glycan structure in Saccharomyces cerevisiae"; Appl Environ Microbiol, Nov. 30, 2012,vol. 79, No. 3, pp. 997-1007.
Orchard et al.: "Rhodanine-3-acetic acid derivatives as inhibitors of fungal protein mannosyl transferase 1 (PMT1)"; Bioorg Med Chem Lett, Aug. 2, 2004, vol. 14, No. 15, p. 3975-3978.
Uniprot: "P38179: Dol-P-Man:Man(5)GlcNAc(2)-PP-Dol alpha-1,3-mannosyltransferase"; May 4, 2016, pp. 1-7. Retrieved from the Internet on Dec. 26, 2017: https://web.archIve.org/web/20160504193836/http://www.uniproLorg/uniprot/P38179>.
Yokoyama et al.: "Taxonomic rearrangement of the genus Schizochytrium sensu lato based on morphology, chemotaxonomic characteristics, and 18S rRNA gene phylogeny (Thraustochytriaceae, Labyrinthulomycetes): emendation for Schizochytrium and erection of Aurantiochytrium and Oblongichytrium gen. nov."; Mycoscience, Aug. 1, 2007, vol. 48, No. 4, pp. 199-211.
Aebi, et al.: "Cloning and Characterization of the ALG3 Gene of Saccharomyces cerevisiae;" Glycobiology, 1996, vol. 6, No. 4, pp. 439-444.
Bayne, et al.: "Vaccination Against Influenza with Recombinant Hemagglutinin Expressed by Schizochytrium sp. Confers Protective Immunity;" PLOS ONE, Apr. 2013, vol. 8, Issue 4, pp. E61790, 2-10.
Bobrowicz, et al.: "Engineering of an Artificial Glycosylation Pathway Blocked in Core Oligosaccharide Assembly in the Yeast Pichia pastoris: Production of Complex Humanized Glycoproteins with Terminal Galactose;"Glycobiology, 2004, vol. 14, No. 9, pp. 757-766.
Choi, et al.: "Use of Combinatorial Genetic Libraries to Humanize N-Linked Glycosylation in the Yeast Pichia pastoris;" PNAS, Apr. 29, 2003, vol. 100, No. 9, pp. 5022-5027.
Geijtenbeek, et al.: "Signalling Through C-Type Lectin Receptors: Shaping Immune Responses;" Nature Reviews | Immunology, Jul. 2009, vol. 9, pp. 465-479.
Hamilton and Gerngross: "Glycosylation Engineering in Yeast: the Advent of Fully Humanized Yeast;"Current Opinion in Biotechnology, 2007, vol. 18, pp. 387-392.
International Search Report dated Jul. 12, 2018 regarding PCT/US2018/030235.
Wildt and Gerngross: "The Humanization of N-Glycosylation Pathways in Yeast;" Nature Reviews | Microbiology, 2005, vol. 3, pp. 119-128.

* cited by examiner

*Primary Examiner* — Maryam Monshipouri
(74) *Attorney, Agent, or Firm* — Wolf, Greenfield & Sacks, P.C.; Karen K. Chan

(57) ABSTRACT

The present invention provides recombinant cells that contain a modification causing altered expression or function of at least one mannosyl transferase enzyme. As a result of the modification the cells produce a glycoprotein or glycopeptide that has an N-linked glycan profile that is simplified or humanized. The glycoprotein or glycopeptide can have at least 25% fewer high mannose structures on than the glycoprotein or glycopeptide produced by a cell that does not have the modification. In some embodiments the modification is a deletion, knock out, or disruption of a gene encoding a mannosyl transferase, which can be in an Alg3 gene. Therefore, the proteins produced avoid many of the problems associated with the therapeutic use of glycoproteins from species having foreign or plant-like patterns of glycosylation. The invention also provides compositions of the glycoproteins or glycopeptides and methods of making them.

29 Claims, 9 Drawing Sheets
Specification includes a Sequence Listing.

| Per-methylated mass (m/z)[1] | Text description of structures | Cartoon representation of structures[2] | % N-linked glycans[3] | |
|---|---|---|---|---|
| | | | PNGaseF | PNGaseA |
| 1171 | Man₃GlcNAc₂ | | 2.75 | n.d. |
| 1579 | Man₅GlcNAc₂ or | | 12.10 | 11.16 |
| 1668 | Sulph₁Man₅GlcNAc₂ or | | 5.14 | 7.01 |
| 1740 | Xyl₁Man₅GlcNAc₂ or | | 3.92 | 2.43 |
| 1783 | Man₆GlcNAc₂ | | 23.8 | 25.96 |
| 1872 | Sulph₁Man₆GlcNAc₂ | | 5.55 | 10.71 |
| 1987 | Man₇GlcNAc₂ | | 17.59 | 16.93 |
| 2033 | Sulph₁Xyl₁Man₆GlcNAc₂ or | | 2.14 | n.d. |
| 2076 | Sulph₁Man₇GlcNAc₂ | | 3.04 | 5.37 |
| 2191 | Man₈GlcNAc₂ or | | 10.12 | 8.26 |
| 2234 | Man₇GlcNAc₃ or | | 4.45 | 3.48 |
| 2395 | Man₉GlcNAc₂ | | 7.16 | 6.17 |
| 2438 | Man₈GlcNAc₃ or | | 2.27 | 1.82 |
| 2642 | Man₉GlcNAc₃ | | n.d. | 0.70 |

[1] All masses (mass+Na) are single-charged.
[2] Structures were assigned based on MS¹ mass, MS² fragmentation (CID) and general biosynthetic pathway of N-glycans
[3] Calculated from the area units of detected N-linked glycans; nd = not detected
Legend – ■ - GlcNAc; ● - Man; □ - HexNAc; ✳ - Pentose; S - Sulfation

FIGURE 7

| Permethyl ated mass (m/z)[1] | Text description of structures | Cartoon representation of structures[2] | % N-linked glycans[3] | |
|---|---|---|---|---|
| | | | PNGaseF | PNGaseA |
| 1171 | Man3GlcNAc2 | | 40.62 | 40.56 |
| 1260 | Sulph1Man3GlcNAc2 | | 40.65 | 39.60 |
| 1375 | Man4GlcNAc2 | | 8.36 | 8.95 |
| 1579 | Man5GlcNAc2 | | 7.64 | 7.44 |
| 1783 | Man6GlcNAc2 | | 2.72 | 2.53 |

[1] All masses (mass+Na) are single-charged.
[2] Structures were assigned based on MS[1] mass, MS[2] fragmentation (CID) and general biosynthetic pathway of N-glycans
[3] Calculated from the area units of detected N-linked glycans; nd = not detected
Legend – ■ - GlcNAc; ● - Man; S - Sulfation

FIGURE 8

SEQUENCE LISTING

<160> NUMBER OF SEQ ID NOS: 5

<210> SEQ ID NO 1
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: #552, i1485, Schizochytrium sp

<400> SEQUENCE: 1

```
Met Lys Phe Ala Thr Ser Val Ala Ile Val Leu Val Ala Asn Val Ala
1               5                   10                  15

Thr Ala Leu Ala Gln Ser Asp Gly Cys Thr Ala Thr Asp Gln
            20                  25                  30
```

<210> SEQ ID NO 2
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: #579, Batrachochytrium dendrobatidis

<400> SEQUENCE: 2

```
Met Pro Phe Asn Arg Leu Ser Leu Pro Cys Leu Leu Leu Ala Leu Ile
1               5                   10                  15

Ala Ser Leu Phe Ile His Ala Ala Gln Ala Gly
            20                  25
```

<210> SEQ ID NO 3
<211> LENGTH: 1305
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SG4EUKT579099, Alg3.1 genefromAurantiochytrium

<400> SEQUENCE: 3

```
atgtctttgc gtgcgagtaa ggatgccctc gtacgtcttc gaggggccct cgacaatgca      60
agcactcagt ggtggtggtg ggccatggca gccacggcag acttggcact tagcctgctt     120
attgtgaaac tcgtgcctta tacggagatc gactttaaag cgtacatgca agaggttgaa     180 ggcccctat tgcatgatga atgggactat acaaagctca ggggcgacac aggcccgctg      240
gtttatcctg ccggttttgt gtatatttat atgggcatcc gctggctcac tgaagacggc     300
acgaacctgt ggcgaggcca gatacttttt gcaagtctgc atgcaattct gtttaccttt    360
gtacttggat ccatatatta ccagccagat gcatcaaaag atcctcgcag agtgccgttc     420
tgggtaggac tctagcagt attatcgaga cgtgtgcatt caatctttgt tctgaggctc       480
ttcaacgacg gcattgctat ggtgtttatg tatgcagcag tatatatgta tgtgcggagg     540
cgttggacgc taggtacggc tttcttcagc gcagcactta gcgtgaaaat gaatatactc    600
ctatttgcgc caggattagc cgtgttgatg ctcgaggcta cgggtttggc gtcgagcata     660
ctgcaggcag tgatctgcgt agcatcacag attgccttag ctttgccgtt cctccaagtc    720
```

| | |
|---|---|
| aacgcagccg ggtatctaaa tcgggctttt gagctaggtc gtgtctttac gtacaaatgg | 780 |
| acagtaaact tcaagtttct cagccctgaa gcttttgtga gtaaggcact tgcccaaggc | 840 |
| ctgctgtctg ccactttact tacatgggtc ggctttgggt ctcgccactt tgcttcctct | 900 |
| cacacaggtg gtcttcgcgg ccttgtgtac acgagcattg ttcgaccact gaaagctccg | 960 |
| cttgaagaca caatttcaac cgtccaaatg catgactgga aacttcacgt tttgacgctc | 1020 |
| ctattcacaa gcaactttat tggcatcgtt tttgcgcgaa gcatccatta ccaattctac | 1080 |
| acttggtact ttcacactgt ctcattctta gtgtacgcca gtggtggaaa cttcgcgttg | 1140 |
| tctcttctta tttgcgtttc tctagaagta tgctttaacg tgtatccttc aacagcagaa | 1200 |
| tcgagtgcta tcttgcaggc aactcatctt gttttgttat tgagacttgc tacacgaaaa | 1260 |
| ccttgcccac ttacagcaca gagcaagcgc cctaaacaag catga | 1305 |

<210> SEQ ID NO 4
<211> LENGTH: 1305
<212> TYPE: DNA
<213> ORGANISM: Artificial Sequence
<220> FEATURE:
<223> OTHER INFORMATION: Synethic
<220> FEATURE:
<221> NAME/KEY: misc_feature
<223> OTHER INFORMATION: SG4EUKT579102, Alg3.2 gene from
      Aurantiochytrium

<400> SEQUENCE: 4

| | |
|---|---|
| atgtctttgc gtgcgagtaa ggatgccctc gtacgtcttc gaggggccct cgacaatgca | 60 |
| agcactcagt ggtggtggtg ggccatggca gccacggcag acttggcact tagcctgctt | 120 |
| attgtgaaac tcgtgcctta tacggagatc gactttaaag cgtacatgca agaggttgaa | 180 |
| ggcccctat tgcatgatga atgggactat acaaagctca ggggcgacac aggcccgctg | 240 |
| gtttatcctg ccggttttgt gtatatttat atgggcatcc gctggctcac tgaagacggc | 300 |
| acgaacctgt ggcgaggcca gatactttt gcaagtctgc atgcaattct tgtttacctt | 360 |
| gtacttggat ccatatatta ccagccagat gcatcaaaag atcctcgcag agtgccgttc | 420 |
| tgggtaggac tctagcagt attatcgaga cgtgtgcatt caatctttgt tctgaggctc | 480 |
| ttcaacgacg gcattgctat ggtgtttatg tatgcagcag tatatatgta tgtgcggagg | 540 |
| cgttggacgc taggtacggc tttcttcagc gcagcactta gcgtgaaaat gaatatactc | 600 |
| ctatttgcgc caggattagc cgtgttgatg ctcgaggcta cgggtttggc gtcgagcata | 660 |
| ctgcaggcag tgatctgcgt agcatcacag attgccttag ctttgccgtt cctccaagtc | 720 |
| aacgcagccg ggtatctaaa tcgggctttt gagctaggtc gtgtctttac gtacaaatgg | 780 |
| acagtaaact tcaagtttct cagccctgaa gcttttgtga gtaaggcact tgcccaaggc | 840 |
| ctgctgtctg ccactttact tacatgggtc ggctttgggt ctcgccactt tgcttcctct | 900 |
| cacacaggtg gtcttcgcgg ccttgtgtac acgagcattg ttcgaccact gaaagctccg | 960 |
| cttgaagaca caatttcaac cgtccaaatg catgactgga aacttcacgt tttgacgctc | 1020 |
| ctattcacaa gcaactttat tggcatcgtt tttgcgcgaa gcatccatta ccaattctac | 1080 |
| acttggtact ttcacactgt ctcattctta gtgtacgcca gtggtggaaa cttcgcgttg | 1140 |
| tctcttctta tttgcgtttc tctagaagta tgctttaacg tgtatccttc aacagcagaa | 1200 |
| tcgagtgcta tcttgcaggc aactcatctt gttttgttat tgagacttgc tacacgaaaa | 1260 |
| ccttgcccac ttacagcaca gagcaagcgc cctaaacaag catga | 1305 |

```
<210> SEQ ID NO 5
<211> LENGTH: 1305
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SG4EUKT561246, Alg3.3 gene from
      Aurantiochytrium

<400> SEQUENCE: 5
atgtctttcc gtgcgagtaa ggatgccctc gtacgtcttc gagggccct cgacaatgca        60 agcactcagt ggtggtggtg ggccatggca gccacggcag acttggcact tagcctgctt      120
attgtgaaac tcgtgcctta tacggagatc gactttaaag cgtacatgca agaggttgaa      180
ggccccctac tgcatgatga atgggactat acaaagctca ggggcgacac aggcccgctg      240
gtttatcctg ctggttttgt gtatatttat atgggcatcc gctggctcac tgaagacggc      300
acaaacctgt ggcgaggcca gatacttttt gcaagtctgc atgcaattct tgtttacctt      360
gtacttggat ccatatacta ccagccagat gcatcaaaag atcctcgcag agtgccgttc      420
tgggtaggac tctagcagt attatcgaga cgtgtgcatt caatctttgt tctgaggctc       480
ttcaacgacg gcattgctat ggtgtttatg tatgcagcag tatatatgta tgtgcggagg      540
cgttggacgc taggtacggc tttcttcagc gcagcactta gcgtgaaaat gaatatactc      600
ctatttgcgc caggattagc cgtgttgatg ctcgaggcta cgggtttggc gtcgagcata      660
ctgcaggcag tgatctgcgt agcatcacag attgccttag ctttgccgtt cctccaagtc      720
aatgcagcag ggtatctaaa tcgggctttt gagctaggtc gtgtctttac gtacaagtgg      780
acagtaaact tcaagtttct cagccctgaa gcttttgtaa gtaaggcact tgcccaaggc      840
ctgctgtctg ccactttact tacatgggtc ggctttgggt ctcgccattt tgcttcctct      900
cacacaggtg gccttcgcgg ccttgtgtac acgagcattg ttcgaccact gaaagctccg      960
cttgaagaca caatttcaac cgtccaaatg catgactgga aacttcacgt tttgacgctc     1020
ctattcacaa gcaactttat tggcatcgtt tttgcgcgaa gcatccatta ccaattctac     1080
acttggtact ttcacactgt ctcattctta gtgtacgcca gtggtggaaa cttcgcgttg     1140
tctcttctta tttgcgtttc tctagaagta tgctttaacg tgtatccttc aacagcagaa     1200
tcgagtgcta tcttgcaggc aactcatctt gttttgttat tgagacttgc tacacgaaaa     1260
ccttgcccac ttacagcaca gagcaagcgc cctaaacaag catga                     1305
```

EXPRESSION OF MODIFIED GLYCOPROTEINS AND GLYCOPEPTIDES

CROSS-REFERENCE TO RELATED APPLICATIONS

This application claims benefit of priority under 35 U.S.C. § 119(e) of U.S. Ser. No. 62/416,086, filed Nov. 1, 2016, the entire contents of which is incorporated herein by reference in its entirety.

FIELD OF THE INVENTION

The invention involves the production of proteins and peptides having humanized or simplified N-glycan patterns, host cells, methods of producing the glycoproteins and glycopeptides, and expression cassettes and other tools useful in the methods.

BACKGROUND OF THE INVENTION

Microbial expression systems have numerous advantages for the production of useful proteins. While certain microbial systems are useful for producing simple proteins, such microbial systems would need to be improved for the efficient production of more complex proteins. The improvement of microbial cell specific productivities requires complex engineering, and substantial understanding and rewiring of the underlying microbial metabolism. An ideal strain would be genetically stable, have a high specific and volumetric productivity, form no by-products, and use a well-defined medium. These characteristics would allow for downstream processing with a limited number of steps.

Labyrinthulomycetes are robustly fermentable eukaryotic microalgae. These heterotrophic microorganisms are recognized for their industrial ability to consume sugar and store large amounts of cellular oils as triglycerides; the most commercially important is docosahexaenoic acid (DHA), an omega-3 polyunsaturated fatty acid (PUFA) that is a major component of fish oil. These organisms produce oils that can be used in human and animal nutritional supplements, as well as for food fortification applications. These triglyceride oils can be produced in culture using inexpensive media.

Because of these desirable qualities it would be advantageous to have recombinant Labyrinthulomycetes cells that are able to produce a variety of proteins or therapeutic proteins, including therapeutic proteins and functional antibodies.

Many therapeutic proteins require N-linked glycosylation to function, optimally. The human pathway for synthesizing N-linked glycans differs from those of other mammals, invertebrates, plants, insects, and lower eukaryotes (such as yeast of fungi). This presents a problem when attempting to express human proteins in heterologous hosts, namely that the protein of interest will not contain human N-linked glycans, but instead be decorated with N-linked glycans that are endogenous to the heterologous host. This can result in a myriad of problems ranging from proteins that are allergenic, less active, inactive, less soluble, insoluble, unstable, unable to properly interact with biological targets. It would therefore be very useful to have a heterologous host system that is able to produce proteins containing human patterns of glycosylation or simplified glycosylation patterns that could be easily converted into human patterns.

SUMMARY OF THE INVENTION

The present invention provides recombinant host cells that contain a genetic modification in one or more genes that encode a mannosyl transferase. As a result of the modification the cells produce a glycoprotein or glycopeptide that has an N-linked glycan profile that is humanized or human-like, or is simplified. In some embodiments the glycoprotein or glycopeptide has at least 25% fewer high mannose N-glycan structures on than the glycoprotein or glycopeptide produced by a cell that does not have the modification. The genetic modification can be a deletion, knock out, or disruption, which can be in the Alg3 gene, and the host cell can be a Labyrinthulomycete cell. Therefore, the proteins produced avoid many of the problems associated with the use of glycoproteins or glycopeptides having patterns of glycosylation of non-human species. The invention also provides compositions of the glycoproteins or glycopeptides, methods of making them, and nucleic acid constructs useful for the methods.

In a first aspect the present invention provides a recombinant cell having a genetic modification of a gene that encodes a mannosyl transferase. The cell produces a glycoprotein or glycopeptide having an N-linked glycan profile that has at least 25% fewer high mannose structures than the N-linked glycan profile from a cell that does not comprise the genetic modification in the gene that encodes the mannosyl transferase, i.e. a reference cell. The genetic modification can be any of a deletion, an insertion, a replacement, or a disruption. In one embodiment the genetic modification is a deletion, the cell is a Labyrinthulomycete cell, and the mannosyl transferase is an alpha-1,3-mannosyl transferase. The mannosyl transferase can be of the class EC 2.4.1.258. In some embodiments the glycoprotein is an antibody, non-limiting examples of which include any of trastuzumab, eculizumab, natalizumab, cetuximab, omalizumab, usteinumab, panitumumab, and adalimumab, or a functional fragment of any of them.

In some embodiments the glycoprotein or glycopeptide has an N-linked glycan profile having at least 50% fewer high mannose N-linked glycans than the N-linked glycan profile from a Labyrinthulomycetes cell that does not comprise the mannosyl transferase deletion, i.e. a reference cell. In other embodiments the glycoprotein or glycopeptide has an N-linked glycan profile having less than 50% high mannose structures. In various embodiments the Labyrinthulomycetes cell can be any of an *Aurantiochytrium*, a *Schizochytrium*, or *Thraustochytrium*. In other embodiments the glycoprotein or glycopeptide can have at least 25% fewer xylose moieties than the cell that does not comprise the mannosyl transferase deletion, or can have no N-linked glycans comprising xylose. In other embodiments the glycoprotein or glycopeptide comprises at least 50% fewer high mannose structures compared to the reference cell. The glycoprotein or glycopeptide can also have at least 25% more paucimannose structures versus the cell that does not comprise the mannosyl transferase genetic modification. In some embodiments more than 50% of the N-linked glycans comprise a paucimannose glycan structure or a man3 glycan structure.

In another aspect the invention provides methods of producing a glycoprotein or glycopeptide that comprises a simplified N-glycan profile. The methods include steps of performing a genetic modification in a gene that encodes a mannosyl transferase in a host cell; cultivating the host cell; and harvesting a glycoprotein or glycopeptide from the cell that has a simplified N-linked glycan profile. The methods can produce any of the glycoproteins or glycopeptides produced by the cells described herein. In the methods the mannosyl transferase can be an alpha-1,3-mannosyl transferase, for example a mannosyl transferase of the class EC 2.4.1.258. The methods can be conducted with Labyrinthulomycete host cell, the genetic modification can be a deletion, and the glycoprotein can be an antibody. Examples of antibodies produced include, but are not limited to, trastuzumab, eculizumab, natalizumab, cetuximab, omalizumab, usteinumab, panitumumab, and adalimumab, or a functional fragment of any of them. In some of the methods the glycoprotein or glycopeptide has at least 50% fewer N-linked glycans compared to a host cell that does not have the mannosyl transferase deletion. The N-linked glycan profile can have less than 50% high mannose structures. The methods can be conducted on any of the host cells described herein, such as a Labyrinthulomycete cell, including *Aurantiochytrium*, *Schizochytrium*, and *Thraustochytrium*. The glycoprotein or glycopeptide can have at least 25% fewer xylose moieties than the cell that does not comprise the mannosyl transferase deletion. The methods can produce a glycoprotein or glycopeptide that does not have N-linked glycans having xylose. The methods can also produce a glycoprotein or glycopeptide that has at least 50% fewer high mannose structures, or a glycoprotein or glycopeptide having at least 25% more paucimannose structures compared to the cell that does not have the mannosyl transferase deletion. The methods can also produce a glycoprotein or glycopeptide where more than 50% of the N-linked glycans are a paucimannose glycan structure or a man3 glycan structure.

In another aspect the invention provides a composition containing a glycoprotein or glycopeptide that has a simplified N-glycan profile. The glycoprotein or glycopeptide can be derived from a recombinant host cell as described herein that has a genetic modification of a gene that encodes a mannosyl transferase. The glycoprotein or glycopeptide of the composition can be any produced by the cells as described herein. In some embodiments the glycoprotein or glycopeptide has at least 25% fewer high mannose structures versus a host cell that does not have the mannosyl transferase genetic modification. The mannosyl transferase can be an alpha-1,3-mannosyl transferase, for example a mannosyl transferase of the class EC 2.4.1.258.

In another aspect the invention provides methods of producing a glycoprotein or glycopeptide having an N-glycan profile comprising at least 25% man3 or man3/man4 glycan structures, but the glycoprotein or glycopeptide produced by the methods can be any described herein. The methods involve providing a recombinant Labyrinthulomycete cell that produces a heterologous glycoprotein or glycopeptide and that also has a mannosyl transferase enzyme. The method involves contacting the recombinant cell with a molecule that reduces mannosyl transferase enzyme activity in the cell, and the cell thereby produces the glycoprotein or glycopeptide. In some embodiments the molecule that reduces the mannosyl transferase activity is an RNAi. The RNAi can be encoded by one or more exogenous nucleic acid(s) comprised within the cell, which can be comprised on a vector or integrated into the genome of the cell. The recombinant cell can also be present within a medium that comprises the RNAi. The molecule can that reduces the mannosyl transferase activity can also be an inhibitor of mannosyl transferase, which also can be produced by one or more nucleic acid molecules comprised in the cell. In various embodiments the inhibitor can be rhodanine-3-acetic acid, or 5-[[3-(1-phenylethoxy)-4-(2-phenylethoxy)phenyl]methylene]-4-oxo-2-thioxo-3-thiazolidineacetic acid (5a). The recombinant cell can also be present within a medium that contains the inhibitor.

In another aspect the invention provides methods of producing a glycoprotein or glycopeptide having an N-glycan profile comprising at least 25% man3 or man3/man4 glycan structures, or any glycoprotein or glycopeptide described herein. The methods involve providing a recombinant Labyrinthulomycete cell that produces a heterologous glycoprotein or glycopeptide, modifying the cell to reduce or inactivate at least one mannosyl transferase enzyme of the cell, and thereby producing the glycoprotein or glycopeptide. Modifying the cell can involve disrupting or deleting a gene encoding the mannosyl transferase enzyme, and/or inactivating the transcription or translation of a gene encoding the mannosyl transferase enzyme. The enzyme can be inactivated by antisense RNA, RNAi, or by a ribozyme, as described herein. The enzyme can also be inactivated by a transcriptional regulator. In one embodiment modifying the cell involves contacting the cell with an inhibitor of mannosyl transferase, which can be any inhibitor or RNA described herein. The inhibitor can be produced one or more nucleic acid molecules contained in the cell. The inhibitor can be any described herein.

In another aspect the invention provides a recombinant cell having at least one modified or deleted mannosyl transferase, and that produces a glycoprotein or glycopeptide having an N-linked glycan profile that has at least 25% fewer high mannose structures than the N-linked glycan profile from a cell that does not comprise the disrupted or deleted mannosyl transferase. The glycoprotein or glycopeptide can also be any described herein.

DETAILED DESCRIPTION OF THE DRAWINGS

FIG. 1 provides a diagram illustrating the types of glycans produced in various types of organisms.

FIG. 2 provides a schematic illustration of ER N-linked glycosylation from *Saccharomyces cerevisiae*.

FIG. 3A provides a graphical illustration of the production of antibody (mg/L), biomass as dry cell weight (g/L) and total FAME (g/L) as part of biomass obtained in a fermentation with the background strain containing Alg3 (Alg3+). FIG. 3B provides the comparative graphical illustration of the fermentation with the modified, Alg3 deletion (Alg3−).

FIG. 4 illustrates the N-linked glycan profile on a specific glycoprotein antibody (trastuzumab) produced by the Alg3+ strain. MALDI-MS results of permethylated glycans released from trastuzumab antibody by PNGaseF produced by the Alg3+ organism. Modification occurred at the N-linked glycopeptide $^{323}$EEQYNSTYR$^{331}$. Legend: ■—GlcNAc (dark square); ●—Man (dark circle); ○—Hex (open circle); □—HexNAc (open square); ☆—Xylose (star); S—Sulfation.

FIG. 5 illustrates the comparative N-linked glycan profile of the same glycoprotein as FIG. 4 but with the Alg3−deletion strain. The resultant profile shows a high preponderance of Man3 glycan structures. Modification occurred at the N-linked glycopeptide $^{323}$EEQYNSTYR$^{331}$. Legend: ■—GlcNAc (dark square); ●—Man (dark circle); ○—Hex (open circle); □—HexNAc (open square); ☆—Xylose (star); S—Sulfation.

FIG. 6A provides a schematic illustration of the structure of man3 glycan structure. FIG. 6B provides a similar illustration of man4.

FIG. 7 shows N-linked glycans from the alg3+ strain detected by MALDI TOF/TOF MS. Structures were assigned based on ESI-MS$^n$ fragmentation of individual peaks.

FIG. 8 shows N-linked glycans from the alg3– strain detected by MALDI TOF/TOF MS and structures were assigned based on ESI-MS$^n$ fragmentation of individual peaks.

DETAILED DESCRIPTION OF THE INVENTION

Figure 1:
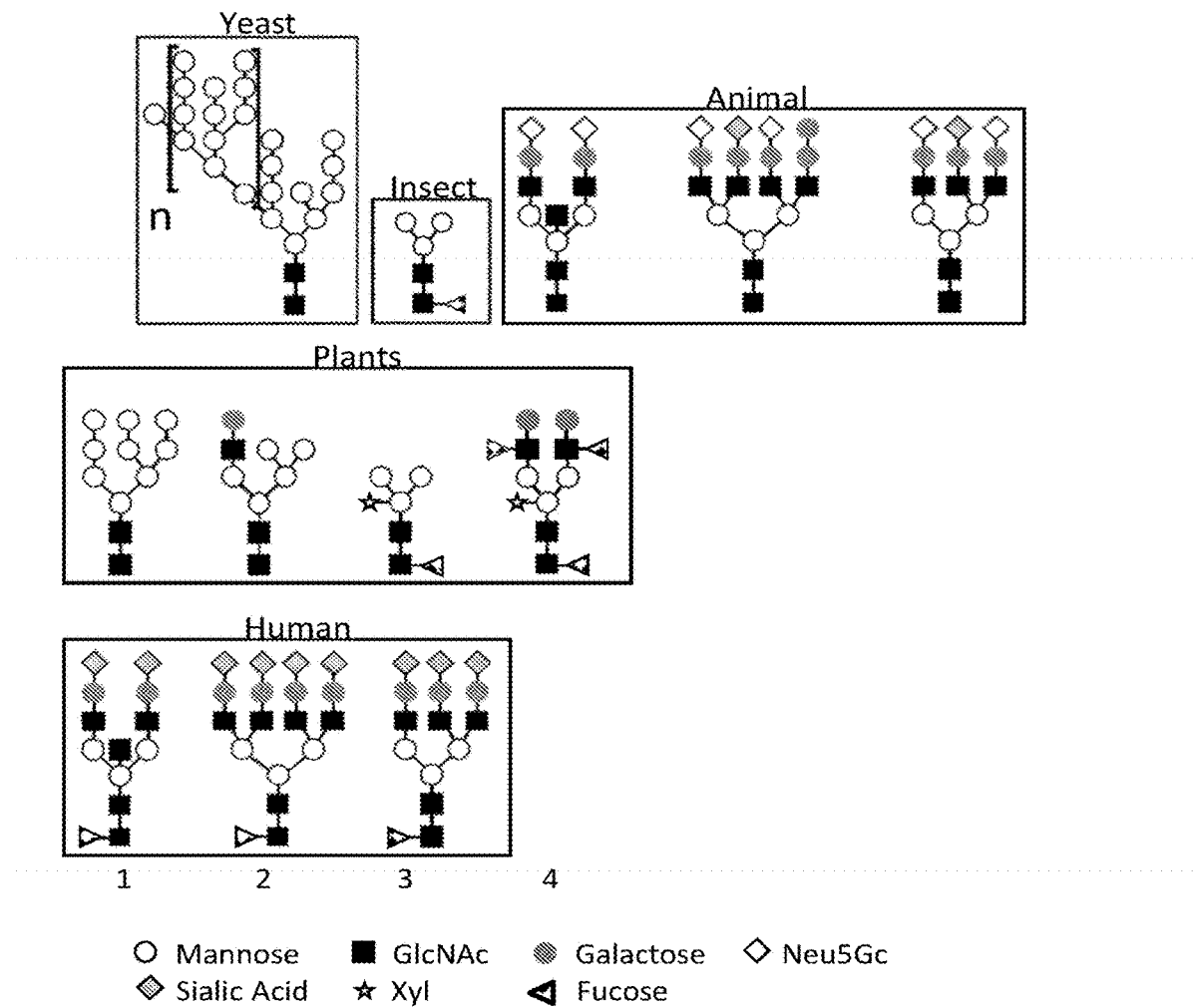

The present invention provides recombinant host cells or organisms that contain a genetic modification that enables the cells or organisms to produce proteins or peptides having humanized or simplified glycosylation patterns, and therefore more acceptable to human patients or easily convertible into human-like glycosylation patterns. The modification can be the functional disruption of a mannosyl transferase activity, e.g. via the deletion of a gene that encodes a mannosyl transferase enzyme. The cells or organisms produce glycoproteins or glycopeptides, for example therapeutic glycoproteins or glycopeptides, that have an N-glycan profile that is humanized and can therefore be used in humans, or is simplified and convertible into a human-like glycosylation pattern. The glycoproteins and glycopeptides can therefore avoid the problems that have been associated with the use of therapeutic proteins produced by heterologous hosts. The glycoproteins or glycopeptides of the invention can therefore be less allergenic, have improved immunological properties, have higher biological activity and stability, be more soluble, and interact more effectively with biological targets.

In some embodiments the recombinant host cells or organisms of the invention are microorganisms of the class Labyrinthulomycetes. The Labyrinthulomycetes are single-celled marine decomposers that generally consume non-living plant, algal, and animal matter. They are ubiquitous and abundant, particularly on dead vegetation and in salt marshes and mangrove swamps. While the classification of the Thraustochytrids and Labyrinthulids has evolved over the years, for the purposes of the present application, "Labyrinthulomycetes" is a comprehensive term that includes microorganisms of the orders Thraustochytrid and Labyrinthulid, and includes (without limitation) the genera *Althornia, Aplanochytrium, Aurantiochytrium, Botyrochytrium, Corallochytrium, Diplophryids, Diplophrys, Elina, Japonochytrium, Labyrinthula, Labryinthuloides, Oblongichytrium, Pyrrhosorus, Schizochytrium, Thraustochytrium,* and *Ulkenia*. In some examples the microorganism is from a genus including, but not limited to, *Thraustochytrium, Labyrinthuloides, Japonochytrium,* and *Schizochytrium*. Alternatively, a host Labyrinthulomycetes microorganism can be from a genus including, but not limited to, *Aurantiochytrium, Oblongichytrium,* and *Ulkenia*. Examples of suitable microbial species within the genera include, but are not limited to: any *Schizochytrium* species, including, but not limited to, *Schizochytrium aggregatum, Schizochytrium limacinum, Schizochytrium minutum, Schizochytrium mangrovei, Schizochytrium marinum, Schizochytrium octosporum,* and any *Aurantiochytrium* species, any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Strains of Thraustochytriales that may be particularly suitable for the presently disclosed invention include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (ATCC 28209); *Schizochytrium limacinum* UFO 32693); *Thraustochytrium* sp. 23B ATCC 20891; *Thraustochytrium striatum* ATCC 24473; *Thraustochytrium aureum* ATCC 34304); *Thraustochytrium roseum*(ATCC 28210; and *Japonochytrium* sp. L1 ATCC 28207. In some embodiments the recombinant host cell of the invention can be selected from an *Aurantiochytrium* or a *Schizochytrium* or a *Thraustochytrium*, or all of the three groups together. The recombinant host cells of the invention can also be a yeast cell, such as a yeast selected from the genus *Saccharomyces* or *Candida* or *Pichia*. The recombinant host cell of the invention can be selected from any combination of the above groups, which are hereby disclosed as every possible combination as if set forth fully herein.

Labyrinthulomycetes produce proteins having a variety of N-linked glycan structures that contain high mannose structures and may also contain xylose or other hexose modifications. The N-glycan profile of glycoproteins produced by the Labyrinthulomycetes is more similar to that plants than humans and some types of glycans produced in different organisms are shown in FIG. 1. Therefore, native glycosylation patterns produced by these organisms are not optimal for a human patient because the glycosylation patterns are associated with the above-mentioned problems.

The modification(s) comprised in the recombinant cells of the invention can include one or more manipulation(s) of a host cell's genome or proteome using the techniques of molecular biology or biotechnology. The modification can change the genetic makeup of the cells, including the transfer of heterologous genes to produce improved or novel organisms. The modification can be a genetic modification such as, for example, the addition, deletion, modification, inactivation, or optimization of one or more genes. When a gene is added it can be a heterologous gene, e.g. a gene and regulatory sequences encoding a heterologous protein or peptide or antibody or immunoglobulin, which can be a functional and/or assembled and can, optionally, be overexpressed in the cell. The protein or peptide can be glycosylated, as described herein. The protein or peptide can be a therapeutic protein or peptide (e.g. an antibody), meaning that it is useful in the treatment or alleviation of any human or animal disease or medical condition.

In some embodiments the modification can be the functional modification of an enzyme. In various embodiments the functional modification can be the modification of one or more enzyme(s) in the glycosylation pathway. A functional modification is a modification that results in the change in the activity of an enzyme. A functional modification can be one or more mutations in the sequence of a gene, which results in an increase or reduction of the activity of the enzyme (e.g. a mannosyl transferase). In some embodiments the enzyme activity can be reduced by at least 10% or at least 15% or at least 20% or at least 25% compared to unmodified enzyme. In other embodiments the functional modification can be the inclusion of a gene that encodes an inhibitor or a suicide substrate directed to the enzyme which is expressed in the organism and binds the enzyme, and thereby inhibits, reduces, or eliminates its activity (by suicide inhibition, as one example).

The cells of the invention can therefore be recombinant cells, which are cells that contain a recombinant nucleic acid. The recombinant nucleic acid can encode a functional protein that is expressed in, and optionally secreted from, the recombinant cell. The term "recombinant" or "engineered" nucleic acid molecule as used herein, refers to a nucleic acid molecule that has been altered through human intervention.

As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule can include any of: 1) a nucleic acid molecule that has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) include conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The invention also provides a recombinant cell having at least one modified or deleted mannosyl transferase that produces a glycoprotein or glycopeptide having an N-linked glycan profile that has at least 25% fewer high mannose core structures than the N-linked glycan profile from a cell that does not comprise the disrupted or deleted mannosyl transferase.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by the manipulation of native sequences, which are therefore then recombinant (e.g. by mutation of sequences, deletions, insertions, replacements, and other manipulations described below). In some embodiments the exogenous or recombinant nucleic acid can express a heterologous protein product. Non-limiting examples of such manipulations include gene knockouts, targeted mutations and gene replacement, gene replacement, promoter replacement, deletions or insertions, disruptions in a gene or regulatory sequence, as well as introduction of transgenes into the organism. For example, a transgenic microorganism can include an introduced exogenous regulatory sequence operably linked to an endogenous gene of the transgenic microorganism. Recombinant or genetically engineered organisms can also be organisms into which constructs for gene "knock down," deletion, or disruption have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome, or on a vector or other nucleic acid construct. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

Glycoproteins and N-Glycan Profile—Human or Simplified

Figure 4:
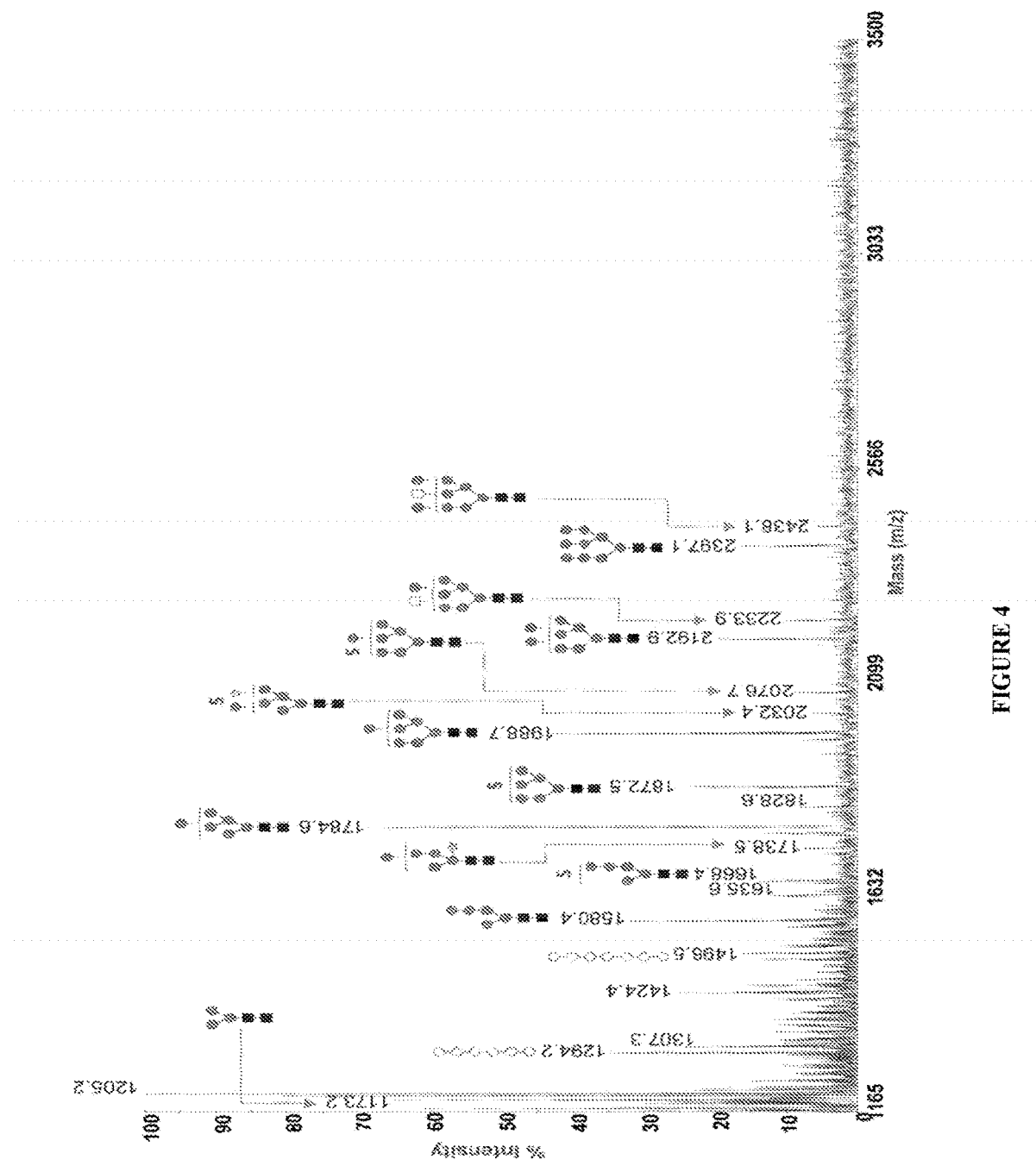
Figure 5:
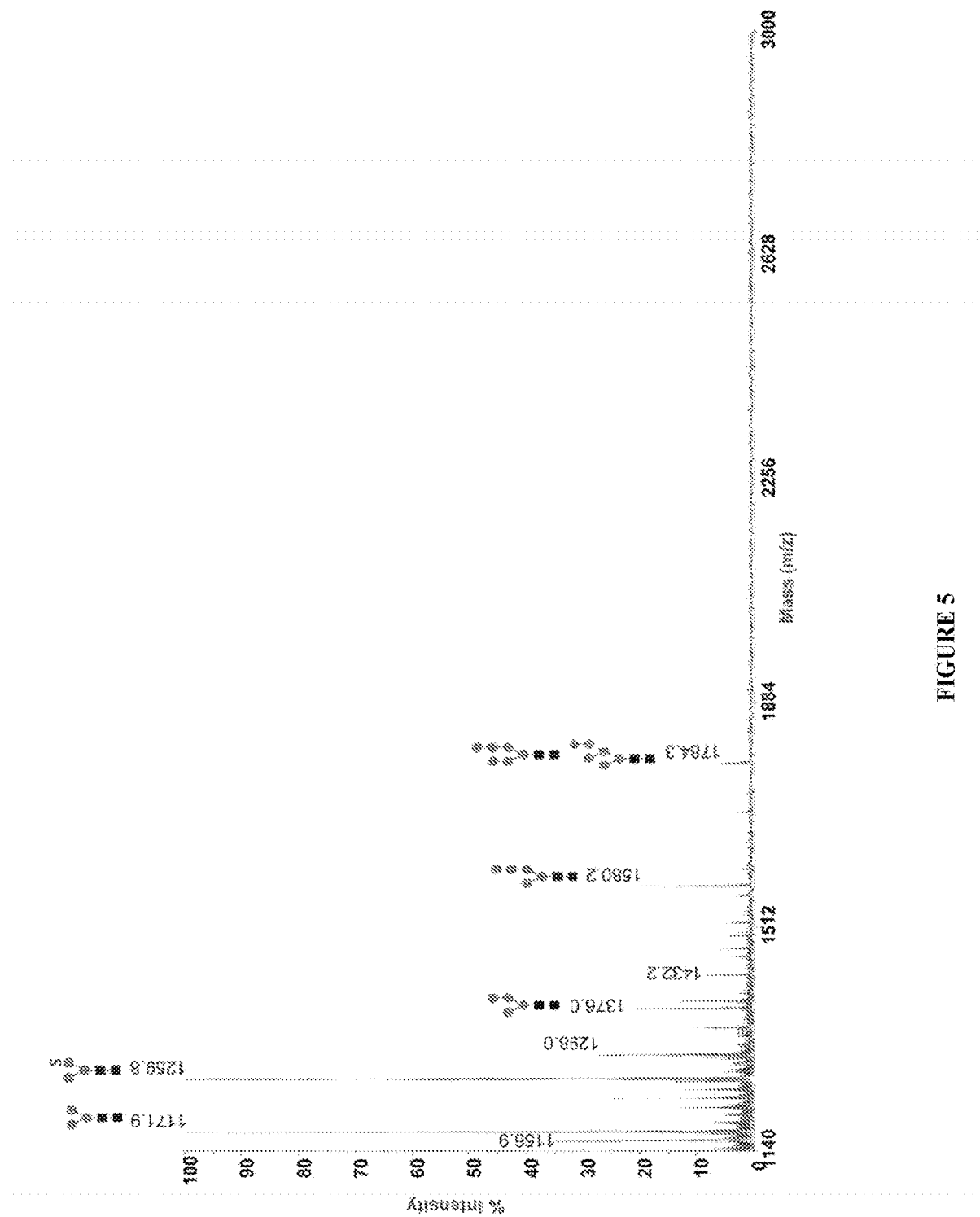

Many proteins produced by living organisms are modified by glycosylation, which occurs in specific patterns depending on the species of organism. These glycosylation patterns are important for their function as cellular recognition signals and to prevent an immune response against the protein, for protein folding, and for stability. N-linked glycan (or N-glycan) profiles refers to the specific glycosylation patterns present on a particular glycoprotein or glycopeptide, or group of glycoproteins or glycopeptides, and they generally vary and are distinguishable between different species, genera, or other taxonomic classifications of organisms. The N-glycan profile of a glycoprotein or glycopeptide describes the number and structure of oligosaccharides that are associated with the particular glycoprotein or glycopeptide. FIGS. 4 and 5 show examples of N-glycan profiles for a specific antibody made in two variants of a specific strain, as well as FIGS. 7 and 8 infra. In some embodiments the glycoprotein produced by the cells of the invention is a glycosylated therapeutic protein, such as a peptide or antibody. Monoclonal antibodies and immunoglobulins are just two of many categories of proteins that the invention can be applied to.

N-linked glycans (or N-glycans) are complex and diverse oligosaccharide chains attached to an asparagine residue of a polypeptide chain. In some embodiments the consensus peptide sequence Asn-X-Thr/Ser is glycosylated, where X is optionally present and can be any amino acid except proline and Thr/Ser is either threonine or serine. Yeast and mammalian biosynthetic pathways of N-linked glycans have been elucidated. The initial steps involve the synthesis of a lipid-linked oligosaccharide precursor structure that is transferred en bloc to nascent proteins in the ER. Typically, transfer of $Glc_3Man_9GlcNAc_2$ to Asn is followed by glucose trimming in the ER. Subsequent cycles of glucose re-addition and removal participate in quality control of protein-folding. The processed high-mannose $GlcNAc_2Man_5$ N-glycan serves as a substrate for the diversification of N-glycans in the Golgi.

Methods of determining the N-glycan profile of a glycoprotein or glycopeptide are known in the art and include, but are not limited to, fluorescently labeling N-glycans that are produced in a method and analyzed using liquid chromatography coupled to fluorescent detection. Methods of determining the N-glycan profile can involve steps of denaturation (e.g. by digestion with trypsin and reduction of disulfide bonds with DTT or mercaptoethanol), deglycosylation (e.g., by treatment with an endoglycosidase (e.g. PNGase) or use of hydrazinolysis or beta-elimination), optional purification (e.g. using a reverse phase C8 and C18 column), optional fluorescent labeling (e.g. using a Schiff base or carbamate), and optional solid phase extraction (e.g. with hydrophilic resins functionalized with amide, diol or microcrystalline cellulose), or analysis using MALDI TOF/TOF and ESI-MS, or MALDI quadrupole ion trap-TOFMS/MS. But persons of ordinary skill understand other methods of determining the N-glycan profile of a glycoprotein or glycopeptide, and the method provided in the examples infra. (e.g. Ex. 9) is one such method that can be applied in the invention, which involves denaturation, deglycosylation (e.g. with PNGaseF and A), and analysis using MALDI TOF/TOF and ESI-MS. Examples of N-glycan profiles analysis are shown in FIG. 4 and FIG. 5. In another embodiment determination of the N-glycan profile can be done by performing deglycosylation with PNGaseF and PNGaseA, followed by MALDI TOF/TOF MS. In a further method, denaturation can be added prior to the deglycosylation step.

Figure 6A:
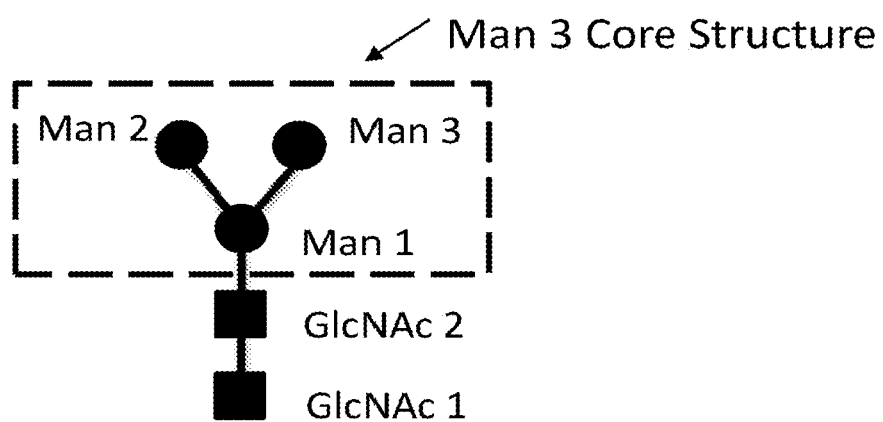
Figure 6B:

By a "high mannose structure" is meant a structure having 5-6 or 5-9 or 5-11 or 5-20 or 5-35 or 5-50 or 10-20 or 10-30 or 10-50 mannose residues, which can also have a GlcNAc$_2$ stem (e.g., see FIG. 1 and FIG. 6). Such embodiments can be represented as, for example, Man$_5$GlcNAc$_2$ or Man$_9$GlcNAc$_2$, or any other symbol indicating 5 or 9 or 5-9 or 5-10 or 5-11 or 5-15 or 5-20 or 5-25 or 5-50 or any number of mannose residues as indicated linked to two GlcNAc, and examples are shown in FIGS. 1 and 4-5. FIG. 1 illustrates some examples of high mannose structures and N-glycan structures in yeast and plant categories. By a molecule having a stated percentage of high mannose structures is meant that, of the total N-glycan structures on the molecule, the stated percentage of the structures are high mannose structure. Thus, when a glycoprotein has less than 50% high mannose structures it is meant that, of the total number of N-glycan structures on the glycoprotein, less than 50% of them contain a high mannose structure. Any of the high mannose structures can be sulfated or unsulfated. N-glycan structures, including high mannose structures, can also contain xylose residues, or other hexose modifications, meaning that one or more of the residues in the structure has a xylose or other hexose residue appended to it, for example as depicted in structures #3 and #4 in the plant N-glycans of FIG. 1. The xylose/hexose modification can be on any of Man1, Man2, or Man3, per FIG. 6 and/or can also be on GlcNAc$_1$ or GlcNAc$_2$. In some embodiments the cells of the invention produce a glycoprotein or glycopeptide having an N-linked glycan profile having at least 10% or at least 15% or at least 20% or at least 25% or at least 30% or at least 35% or at least 40% or at least 45% or at least 50% or at least 60% or at least 70% or at least 80% fewer high mannose structures compared to the same glycoprotein or glycopeptide produced by a reference cell. A reference cell can be a cell of the same cell line that produces the glycoprotein or glycopeptide of interest under the same conditions but does not contain a further genetic modification causing or affecting the observed effect, such as a deletion, knock out, disruption, replacement, etc. In various embodiments the observed effect can be a reduction or other change in high mannose structures, or can be an increase in Man3 and/or Man4 structures, or similar, on the glycoprotein or glycopeptide of interest. In another embodiment the cells of the invention produce a glycoprotein or glycopeptide having an N-linked glycan profile having at least 10% or at least 20% or at least 30% or at least 40% or at least 50% or at least 60% or at least 70% more Man3 and/or Man4 structures compared to the glycoprotein or glycopeptide produced by an organism not containing the genetic modification, i.e. a reference cell. In another embodiment the cells of the invention produce a glycoprotein or glycopeptide that has an N-linked glycan profile having more than 40% or more than 50% or more than 60% or more than 70% or more than 75% or more than 80% or more than 85% or more than 90% Man3 and/or Man4 glycans. Man3 and/or Man4 glycan structures are designated paucimannose and are illustrated in FIGS. 6a and 6b. Thus, paucimannose structures have the structure Man3GlcNAc2 or Man4GlcNAc2, with or without the xylose, fucose, or other hexose modifications described above. Glycans can contain these core structures and also have additional oligosaccharide residues (e.g. GlcNAc, galactose, sialic acid, or fucose), and some exemplary structures are illustrated in FIG. 1. In other embodiments the cells can reduce the high mannose structures as described herein and also increase the Man3 and/or Man4 structures as described herein—i.e. the reduction in high mannose structures can be accompanied by the increase in Man3 and/or Man4 structures.

Glycoproteins and glycopeptides that are useful in biologics for use in humans can be those that have N-glycan profiles that are simplified or humanized. Glycoproteins and glycopeptides that have a simplified N-glycan profile are also useful as they can be an effective starting point for the synthesis of more complex humanized N-glycan structures. Simplified N-glycan structures are man3, or man3 and man4 together (man3/man4), structures attached to the GlcNAc2 stem, as illustrated in FIG. 6a-b. These simplified structures can also, optionally, contain a fucose residue attached to any of the mannose or GlcNAc residues. These structures can also be sulfated or unsulfated on any residue. These structures can also lack xylose on any residue or all residues, and can also lack any other hexose modification on any residue or all residues.

Human glycosylation patterns commonly include man3 or man3/man4 glycan structures attached to the GlcNAc2 stem, and can also have any one or more of 1) three or four additional GlcNAc residues present on man2 or man3; 2) 2, 3, or 4 galactose residues present on the GlcNAc residues; 3) 2, 3, or 4 sialic acid residues present on the galactose residues; and optionally N-acetyleuramic acid (Neu5Gc) residues present on the galactose residues. These embodiments are illustrated in FIG. 1. In various embodiments more than 20% or more than 25% or more than 30% or more than 40% or more than 50% or more than 60% or more than 70% or more than 80% or more than 90% or 50-70% or 50-90% or 60-70% or 70-80% or 60-90% of the N-glycan structures on the glycoproteins or glycopeptides produced by the cells of the invention are simplified N-glycan structures. Any of the glycoproteins or glycopeptides produced according to the invention can also lack xylose or another hexose on Man1, Man2, Man3, Man4 (if present), GlcNAc1, or GlcNAc2 (FIG. 6), or contain no residues modified with xylose or another hexose. The simplified glycoprotein or glycopeptide may or may not contain a fucose residue, which if present can be appended to the first or second GlcNAc on the stem. High mannose structures and simplified (e.g. Man3 and/or Man4) structures can be sulfated or unsulfated. The glycoproteins or glycopeptides produced can be useful themselves, or be useful as precursors for further glycol-engineering to further modify the N-glycan profile, for example to further humanize it or make it closer to a human pattern.

Nucleic Acid Constructs

Nucleic acids encoding the heterologous glycoproteins or glycopeptides produced by the cells of the invention can be integrated into the genome of the organism. They can also be expressed from an expression cassette or other nucleic acid construct present in the cell as are known in the art, and which can be transformed into the cell. Examples include, but are not limited to, a plasmid, cosmid, virus, autonomously replicating polynucleotide molecule, phage, linear or circular single-stranded or double-stranded nucleic acid molecule, artificial chromosome, or other nucleic acid construct, DNA or RNA polynucleotide molecule, derived from any source, capable of genomic integration or autonomous replication, comprising a nucleic acid molecule where one or more nucleic acid sequences has been linked in a functionally operative manner, i.e. operably linked. Constructs used in the cells of the invention can also be non-naturally occurring (i.e., non-native). Thus, in one embodiment a gene encoding a heterologous glycoprotein or glycopeptide is expressed from a nucleic acid construct. In other embodiments the gene encoding a heterologous glycoprotein or glycopeptide is integrated into the chromosome of the cell. The gene can also include regulatory sequences, for example a promoter and terminator, and can be inducible. The regulatory sequences can be heterologous or natural regulatory sequences in the cell. Inducible promoters may activate or increase transcription in response to an inducing agent. In contrast, the rate of transcription of a gene under control of a constitutive promoter is not dependent on an inducing agent. A constitutive promoter can be made a conditional or inducible promoter by the addition of sequences that confer responsiveness to particular conditions or to an inducing agent, as known in the art. Thus, promoters may be constitutive or may be inducible or conditional. Promoters or portions of promoters may also be combined in series to achieve a stronger level of expression or a more complex pattern of regulation, as known in the art.

The term "expression cassette" as used herein, refers to a nucleic acid construct that encodes a functional protein or functional RNA operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc. The present invention provides numerous examples of expression cassettes useful for producing the cells and proteins of the invention, and for use in the methods of the invention. The expression cassettes can be comprised in any construct operable in the host cells being utilized. Generally an expression cassette will comprise a promoter, an open reading frame (ORF) encoding the heterologous protein of interest, and a terminator. Additional features can include 3' and 5' homology arms from genomic DNA of the host cell. These can be useful for inserting or integrating the expression cassette at a specific locus in the genome of the cell. Any of the components or features of the expression cassette can be active in any of the host cells described herein.

As used herein, "exogenous" with respect to a nucleic acid or gene indicates that the nucleic or gene has been introduced ("transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

As used herein, "expression" refers to the process of converting genetic information of a polynucleotide into RNA through transcription, which is typically catalyzed by an enzyme, RNA polymerase, and, where the RNA encodes a polypeptide, into protein, through translation of mRNA on ribosomes to produce the encoded protein.

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "heterologous" when used in reference to a polynucleotide, a gene, a nucleic acid, a polypeptide, a protein, or an enzyme, refers to a polynucleotide, gene, a nucleic acid, polypeptide, protein, or an enzyme that is not derived from the host species. For example, "heterologous gene" or "heterologous nucleic acid sequence" as used herein, refers to a gene or nucleic acid sequence from a different species than the species of the host organism it is introduced into. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. Similarly, when referring to a protein localization sequence or protein domain of an engineered protein, "heterologous" means that the localization sequence or protein domain is derived from a protein different from that into which it is incorporated by genetic engineering.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrRNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

The nucleic acid molecules of the present disclosure will preferably be "biologically active" with respect to either a structural attribute, such as the capacity of a nucleic acid molecule to hybridize to another nucleic acid molecule, or the ability of a nucleic acid sequence to be recognized and bound by a transcription factor (or to compete with another nucleic acid molecule for such binding).

Nucleic acid molecules of the present disclosure include nucleic acid sequences of any length, including nucleic acid molecules that are preferably between about 0.05 kb and about 300 kb, or for example between about 0.05 kb and about 250 kb, or between about 0.05 kb and about 150 kb, or between about 0.1 kb and about 150 kb, or for example between about 0.2 kb and about 150 kb, about 0.5 kb and about 150 kb, or about 1 kb and about 150 kb.

The term "operably linked", as used herein, denotes a functional linkage between two or more sequences. For example, an operable linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous. Further, when used to refer to the joining of two protein coding regions, by "operably linked" is intended that the coding regions are in the same reading frame.

The terms "promoter", "promoter region", or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked polynucleotide molecule such as, for example, a coding sequence of a polypeptide or a functional RNA sequence. Promoters may contain, in addition to sequences recognized by RNA polymerase and, preferably, other transcription factors, regulatory sequence elements such as cis-elements or enhancer domains that affect the transcription of operably linked genes. A "Labyrinthulomycetes promoter" as used herein refers to a native or non-native promoter that is functional in Labyrinthulomycetes cells.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. A recombinant cell contains a recombinant nucleic acid.

When applied to organisms, the terms "transgenic" "transformed" or "recombinant" or "engineered" or "genetically engineered" refer to organisms that have been manipulated by introduction of an exogenous or recombinant nucleic acid sequence into the organism. Non-limiting examples of such manipulations include gene knockouts, targeted mutations and gene replacement, promoter replacement, deletion, or insertion, as well as introduction of transgenes into the organism. For example, a transgenic microorganism can include an introduced exogenous regulatory sequence operably linked to an endogenous gene of the transgenic microorganism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

"Regulatory sequence", "regulatory element", or "regulatory element sequence" refers to a nucleotide sequence located upstream (5'), within, or downstream (3') of a polypeptide-encoding sequence or functional RNA-encoding sequence. Transcription of the polypeptide-encoding sequence or functional RNA-encoding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from untranslated regions (UTRs) from a particular polynucleotide sequence. Any of the regulatory elements described herein may be present in a chimeric or hybrid regulatory expression element. Any of the regulatory elements described herein may be present in a recombinant construct of the present disclosure.

The term "terminator" or "terminator sequence" or "transcription terminator", as used herein, refers to a regulatory section of genetic sequence that causes RNA polymerase to cease transcription.

The term "transformation", "transfection", and "transduction", as used interchangeably herein, refers to the introduction of one or more exogenous nucleic acid sequences into a host cell or organism by using one or more physical, chemical, or biological methods. Physical and chemical methods of transformation include, by way of non-limiting example, electroporation and liposome delivery. Biological methods of transformation include transfer of DNA using engineered viruses or microbes (for example, *Agrobacterium*).

Genetic Modifications

Figure 2:
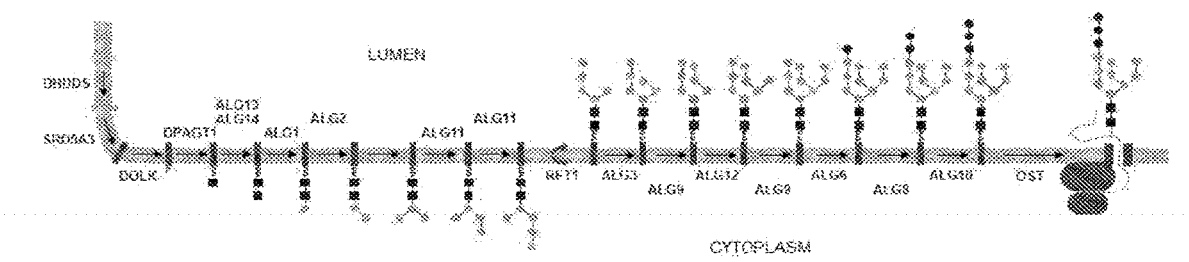

In some embodiments the cells of the invention comprise a genetic modification that causes a change in the N-glycan profile of glycoproteins or glycopeptides produced by the cell. In various embodiments the modification can be a gene knockout, a deletion, a disruption, a mutation (e.g. a point mutation), a rearrangement, a replacement, a suppressor mutation, a targeted mutation, a replacement, a mis-sense mutation, a deletional insertion, a substitution, or an insertion, any of which can be in combination with the introduction of heterologous genes into the organism. In some embodiments the genetic modification is done on a gene that encodes a mannosyl transferase. In some embodiments the gene can encode an enzyme of the class EC 2.4.1.258, which are alpha 1,3-mannosyl transferases. These enzymes catalyze the first ER luminal step of N-linked glycosylation as illustrated in FIG. 2. In other embodiments the gene can encode an alpha-3,3-mannosyl transferase. A gene is considered deleted, disrupted, inactivated, or knocked out when it is either no longer expressed, or has been modified so that it no longer produces a product having the function of the product of the natural gene. In another embodiment the modification can result in a functional reduction of activity in a particular gene, such as a mannosyl transferase as described herein. By functional reduction of activity is meant that the activity of the enzyme encoded by the gene is reduced, and the reduction can be due to a change in the sequence of the encoded gene (i.e. a mutation of one or more genes). The functional reduction of activity of one or more mannosyl transferase genes can also be performed by performing a genetic modification in a regulatory sequence (e.g. a promoter) for one or more mannosyl transferase genes, which thus causes a functional reduction in mannosyl transferase activity, for example by inhibiting transcription or expression of the gene(s). The genetic modification of the regulatory sequence can be any of the same modifications described herein, for example a mutation, deletion, disruption or other modification of one or more promoters controlling expression of one or more mannosyl transferase gene(s).

Mannosyl Transferase Family

The mannosyl transferase genes modified in the invention can be an alpha-1,2-mannosyl transferase, or an alpha-1,3-mannosyltransferase, or an alpha-1,6-mannosyltransferase. In some embodiments the cells and methods of the invention comprise a deletion, knock out, disruption, or other genetic modification described herein to a gene that is a member of the mannosyl transferase gene family. Members of this family include, but are not limited to, Alg1, Alg2, Alg3, Alg6, Alg8, Alg9, Alg10, Alg11, Alg13, and Alg14. The deletion or knock out or other genetic modification can be present in any one or more of the mannosyl transferase genes. These genes can be present as more than one copy and the cells and methods can have the genetic modification to all copies of the gene. In one embodiment the deletion or knock out is of one or more Alg3 gene(s), which encodes an enzyme that catalyzes the addition of the first dol-P-Man derived mannose in an alpha-1,3 linkage to Man5GlcNAc2-PP-Dol. Genes that are members of the Alg3 sub-family encode an alpha-1,3-mannosyl transferase and are found in fungi, mammals, yeast, Labyrinthulomycetes (e.g. *Schizochytrium, Aurantiochytrium, Thraustochytrium*, and other Labyrinthulomycetes), and a wide variety of other organisms. In a specific embodiment the modification is a deletion or knock out or disruption of one or more Alg3 gene(s), which can be done in a host cell that is a Labyrinthulomycete, such as a *Schizochytrium* or *Aurantiochytrium*. Some cells contain more than one Alg3 gene and the deletion, knock out, or disruption can be in any one or more of the Alg3 genes, or all of the Alg3 genes.

It was discovered that the deletion, disruption, or knock out of Alg3 in a Labyrinthulomycete (e.g. an *Aurantiochytrium, Schizochytrium*, or *Thraustochytrium*) resulted in production of a glycosylated protein or peptide having an N-glycan profile that was simplified or humanized, e.g. having a Man3 and/or Man4 structure. The deletion, knock out, or disruption of the Alg3 gene in yeast results in accumulation of lipid-linked oligosaccharides with five mannose residues. Thus, it was an unexpected discovery that deletion, knock out, or disruption of an Alg3 gene in a Labyrinthulomycete resulted in a more desirable simplified N-glycan profile of glycoproteins or glycopeptides synthesized by the host cell, such as having a Man3/Man4 structure.

In some embodiments the glycoprotein or glycopeptide produced by the cells of the invention can be a therapeutic protein or peptide, e.g. enzymes, Ig-Fc-Fusion proteins, or an antibody. The antibody can be a functional antibody or a functional fragment of an antibody. In various embodiments the antibody can be alemtuzumab, denosumab, eculizumab, natalizumab, cetuximab, omalizumab, ustekinumab, panitumumab, trastuzumab, belimumab, palivizumab, natalizumab, abciximab, basiliximab, daelizumab, adalimumab (anti-TNF-alpha antibody), tositumomab-I131, muromonab-CD3, canakinumab, infliximab, daclizumab, tocilizumab, thymocyte globulin, anti-thymocyte globulin, or a functional fragment of any of them. The glycoprotein can also be alefacept, rilonacept, etanercept, belatacept, abatacept, follitropin-beta, or a functional fragment of any of them. The antibody can also be any anti-TNF-alpha antibody or an anti-HER2 antibody, or a functional fragment of any of them. The glycoprotein can be an enzyme, for example idursulfase, alteplase, laronidase, imiglucerase, agalsidase-beta, hyaluronidase, alglucosidase-alpha, GalNAc 4-sulfatase, pancrelipase, DNase, Each of these proteins is an antibody and a therapeutic protein, as well as a monoclonal antibody. A functional antibody or antibody fragment is a molecule that is an antibody or antibody fragment that binds to a target epitope and thereby produces a desired response, for example a biological response or action, or the cessation of a response or action). The desired response can be the same as the response to a natural antibody, but the response can also be to mimic or disrupt the natural biological effects associated with ligand-receptor interactions. When the protein is a functional antibody fragment it can comprise at least a portion of the variable region of the heavy chain, or can comprise the entire antigen recognition unit of an antibody, and therefore can perform the antigen binding properties that are similar to or the same in nature and affinity to those of the complete antibodies. In various embodiments a functional fragment can comprise at least 10% or at least 20% or at least 30% or at least 50% or at least 60% or at least 70% or at least 80% or at least 90% of the native antibody sequence. Any of the recombinant cells disclosed herein can comprise a nucleic acid encoding a functional and/or assembled antibody molecule described herein, or a functional fragment thereof. In various embodiments the therapeutic peptide can be hormones, human growth hormone, leutinizing hormone, thyrotropin-alpha, interferon, darbepoetin, erythropoietin, epoetin-alpha, epoetin-beta, FS factor VIII, Factor VIIa, Factor IX, anithrombin/ATIIcytokines, clotting factors, insulin, erythropoietin (EPO), glucagon, glucose-dependent insulinotropic peptide (GIP), cholecystokinin B, enkephalins, and glucagon-like peptide (GLP-2) PYY, leptin, and antimicrobial peptides.

Promoters and Terminators

The recombinant cell or organism of the invention can be any suitable organism but in some embodiments is a Labyrinthulomycetes cell, and the promoter (and terminator) can be any suitable promoter and/or terminator. Promoters and/or terminators can be used in any combination. For example, any promoter described herein or other promoters that may be isolated from or functional in Labyrinthulomycetes or derived from such sequences can be used in combination with any terminator described herein or other terminators functional in the recombinant cell or organism, or derived from such sequences. For example, terminator sequences may be derived from organisms including, but not limited to, heterokonts (including Labyrinthulomycetes, fungi, microalgae, algae, and other eukaryotic organisms. In various embodiments the promoter and/or terminator is any one operable in a cell or organism that is a Labyrinthulomycetes, including any genus thereof. Any of the constructs can also contain one or more selection markers, as appropriate. A large number of promoters and terminators can be used with the host cells of the invention. Those described herein are examples and the person of ordinary skill with resort to this disclosure will realize or be able to identify other promoters useful in the invention. Examples of promoters include the alpha-tubulin promoter, the TEFp promoter, Hsp60-788 promoter, Tsp-749 promoter, Tubα738 promoter, Tuba-997 promoter, a promoter from the polyketide synthase system, and a fatty acid desaturase promoter. Examples of useful terminators include pgk1, CYC1, and eno2. Promoters and terminators can be used in any advantageous combination and all possible combinations of promoters and terminators are disclosed as if set forth fully herein.

In some embodiments the expression cassettes of the invention comprise one or more of 1) one or more signal sequences; 2) one or more promoters; 3) one or more terminators; and 4) an exogenous sequence encoding one or more proteins, which can be a heterologous protein; 4) optionally, one or more selectable markers for screening on a medium or a series of media. These components of an expression cassette can be present in any combination, and each possible sub-combination is disclosed as if fully set forth herein. In specific embodiments the signal sequences can be any described herein, but can also be other signal sequences. Various signal sequences for a variety of host cells are known in the art, and others can be identified with reference to the present disclosure and which are also functional in the host cells. In exemplary specific embodiments the promoter can be an alpha-tubulin promoter or TEFp, with alpha-tubulin promoter being the weaker of the two. The promoters can be paired with any suitable terminator, but in specific embodiments the tubαp can be paired with the pgk1t terminator. In another embodiment the TEFp promoter can be paired with the eno2 terminator, both terminators being from *Saccharomyces cerevisiae* and also being functional in Labyrinthulomycetes. The selectable marker can be any suitable selectable marker or markers but in specific embodiments it can be nptII or hph. In one embodiment nptII can be linked to the heavy chain constructs and hph can be linked to the light chain constructs.

The present invention also provides a nucleic acid construct or disruption cassette for performing a deletion, knock out, or disruption in a gene that encodes a mannosyl transferase. The nucleic acid construct can be regulated by a promoter sequence and, optionally, a terminal sequence functional in a host cell. The host cell can comprise an expression cassette and also a deletion, knock out, or disruption cassette as disclosed herein, which can also be a CRISPR/Cas 9 cassette that can delete any one or more of the target genes as disclosed herein. In any of the embodiments the host cell can be a Labyrinthulomycetes, such as an *Aurantiochytrium*, a *Schizochytrium*, or a *Thraustochytrium*. The construct or cassette can also have a sequence encoding 5' and 3' homology arms to the gene encoding a mannosyl transferase, such as a 1,3-mannosyl transferase (e.g., one or more Alg3 genes). The construct can also have a selection marker, which in one embodiment can be nat, but any appropriate selection marker can be used.

Methods

The invention also provides methods of producing glycoproteins and glycopeptides in host cells (e.g. Labyrinthulomycetes) that have an N-glycan profile that is simplified or humanized, as described herein. The methods can involve any one or more steps of: transforming a host cell with an expression vector or linear nucleic acid encoding a heterologous glycoprotein or glycopeptide for expression from the vector or integration into the chromosome of the cell, a step of a transforming the host cell with a deletion, knock out, or disruption cassette, a step of deleting or knocking out or disrupting one or more gene(s) that encodes a mannosyl transferase, as disclosed herein, cultivating the cell, and harvesting a glycoprotein or glycopeptide that has an N-glycan profile described herein.

The invention also provides methods of producing a glycoprotein or glycopeptide described herein. The methods involve providing a recombinant Labyrinthulomycete cell that produces a heterologous glycoprotein or glycopeptide and that has a mannosyl transferase enzyme, and contacting the recombinant cell with a molecule that reduces mannosyl transferase enzyme activity in the cell to thereby produce the glycoprotein or glycopeptide having an N-glycan profile comprising at least 25% man3 or man3/man4 glycan structures. The N-glycan profile of the glycoprotein or glycopeptide produced can be any as described herein.

The invention also provides a method of producing a glycoprotein or glycopeptide having an N-glycan profile, such as any disclosed herein. The method involves providing a recombinant Labyrinthulomycete cell that produces a heterologous glycoprotein or glycopeptide, modifying the Labyrinthulomycete cell to reduce or inactivate at least one mannosyl transferase enzyme of the cell, and producing the glycoprotein or glycopeptide. Modifying the cell can involve disrupting or deleting a gene encoding the mannosyl transferase enzyme. In various embodiments the cell is modified by inactivating the transcription or translation of a gene encoding one or more mannosyl transferase enzyme(s), or by contacting the Labyrinthomycete cell with an inhibitor of mannosyl transferase. In another embodiment the mannosyl transferase enzyme can be inactivated by contacting the enzyme with antisense RNA, RNAi, or a ribozyme. The one or more mannosyl transferase enzyme(s) can also be inactivated by a transcriptional regulator. The inhibitor can be produced by one or more nucleic acid molecules comprised in the cell or by any method described herein. And the inhibitor can be any described herein.

Enzyme Inhibition

In some embodiments the activity of the mannosyl transferase can be inhibited, reduced, or eliminated through the use of RNA interference (RNAi) to inhibit the expression of one or more genes encoding a mannosyl transferase. The mannosyl transferase inhibited can be any as described herein. mutating, or can be a separate gene that, when expressed, binds to the enzyme or otherwise causes a reduction in activity of the enzyme. The RNAi suppression of a gene can be accomplished by methods known in the art including, but not limited to, the use of antisense RNA, a ribozyme, small interfering RNA (siRNA) or microRNA (miRNA). The siRNA or miRNA can be transcribed from a nucleic acid inserted into the genome of the cell, or can be transcribed from a plasmid or other vector transformed into the cell, or can be provided in a growth medium in which the cell is comprised.

In other embodiments the activity of the mannosyl transferase enzyme can be inhibited by the use of an enzyme inhibitor. The inhibitor can be a glycosylation inhibitor, and can be an inhibitor of mannosyl transferase or another enzyme in the glysosylation pathway. In various embodiments the inhibitor can be rhodamine-3-acetic acid or 5-[[3-(1-phenylethoxy)-4-(2-phenylethoxy)phenyl]methylene]-4-oxo-2-thioxo-3-thiazolidineacetic acid (5a). In other embodiments the inhibitor can be a protein or peptide inhibitor. In other embodiments the inhibitor can be brefeldin A, 6-diazo-5-oxo-L-norleucine, fructose-6-phosphate amidotransferase, chlorate, 2-deoxyglucose, 3-deoxy-3-fluoroglucosamine, 4-deoxy-4-fluoroglucosamine, 2-deoxy-2-fluoroglucose, 2-deoxy-2-fluoromannose, a plant alkaloid (e.g. castanospermine, australine, deoxynojirimycin, swainsonine, or alkylated or acetlated analogs of them). Persons of ordinary skill with resort to this disclosure will realize additional inhibitors that are useful in the invention. The enzyme inhibitors can be produced by nucleic acids inserted into the genome of the cell, or can be produced from nucleic acids present on a plasmid or other vector transformed into the cell, or can be included in a growth medium in which the cell is grown. The inhibitor can also be an antibody directed to one or more epitopes on the enzyme, or on a substrate for the enzyme.

Compositions

The present invention also provides compositions having a glycoprotein or glycopeptide that has a humanized or simplified N-glycan profile as described herein and is derived from a recombinant Labyrinthulomycete cell described herein. Derived from a cell means that the glycoprotein or glycopeptide was synthesized by the cell. In some embodiments the entire glycoprotein or glycopeptide was synthesized by the cell, including the glycan portion. In some embodiments the glycoprotein or glycopeptide synthesized by the cell comprises more than 25% or more than 50% or all of the glycoprotein or glycopeptide in the composition. The cell can comprise a genetic modification in a gene that encodes a mannosyl transferase, as described herein. In one embodiment the genetic modification is a deletion in an Alg family gene, such as Alg3. The composition can be any of the compositions derived from host cells, as described herein.

Example 1—Trastuzumab Expression

Constructs: PCAB056, 057, 060, 061

This example discloses specific expression constructs that can be applied in the present invention, but persons of ordinary skill with resort to this disclosure will realize many other constructs and variations of those here that can be utilized. Specific constructs pCAB056, 057, 060, and 061 are described in Table 1, which are disclosed with signal peptides. While specific signal peptides are provided herein other signal peptide can be utilized in the invention.

Construct pCAB056 contains the trastuzumab (or HERCEPTIN®) light chain with SEQ ID NO: 1, a signal peptide (#552), expressed from the TEF promoter. This cassette also carries a marker (hph) encoding resistance to hygromycin B. Construct pCAB057 contains the trastuzumab light chain with SEQ ID NO: 2, a signal peptide (#579), expressed from the TEF promoter. This cassette also carries a marker (hph) encoding resistance to hygromycin B. Construct pCAB060 contains the trastuzumab heavy chain with, a signal peptide (#552), expressed from the TEF promoter. This cassette also carries a marker (nptII) encoding resistance to paromomycin. Construct pCAB061 contains the trastuzumab heavy chain with a signal peptide (#579) expressed from the TEF promoter. This cassette also carries a marker (nptII) encoding resistance to paromomycin. In view of this disclosure the constructs can be synthesized through ordinary means. In other embodiments the constructs can use other promoters, as described herein. Examples of useful terminators include pgk1, CYC1, and eno2, any of which can be paired with other markers.

TABLE 1

Summary of trastuzumab expression constructs

| Construct | Promoter | Signal peptide | Gene | Marker |
|---|---|---|---|---|
| pCAB056 | TEF | SP552 SEQ ID NO: 1 | trastuzumab light chain | hph |
| pCAB057 | TEF | SP579 SEQ ID NO: 2 | trastuzumab light chain | hph |
| pCAB060 | TEF | SP552 | trastuzumab heavy chain | nptII |
| pCAB061 | TEF | SP579 | trastuzumab heavy chain | nptII |

Example 2—Construction of Trastuzumab-Producing Strains (5942, 5950, and 5951)

Trastuzumab (HERCEPTIN®) was produced by co-transforming a wild type *Aurantiochytrium* cell #6267 with a pool of DNA comprised of linearized versions of pCAB056, 057, 060 and 061 from Example 1. Transformants that were resistant to both hygromycin B and paromomycin were screened by ELISA for production of antibody. Each clone was cultured overnight in 3 ml FM2 (17 g/L sea salt, 10 g/L yeast extract, 10 g/L peptone, 20 g/L dextrose) in a 24-well plate. They were then diluted 1000× into fresh FM2 (3 mL) and incubated for about 24 hours. The cells were pelleted by centrifugation and the supernatants were assayed using a heavy chain capture/light chain detect sandwich ELISA. The transformants were also screened by colony PCR to determine which signal peptides were present in the top producing clones. The strains with the 3 highest trastuzumab titers measured by sandwich ELISA are shown in Table 2. Diagnostic PCR revealed which signal peptides were linked to the heavy and light chains present in these strains (Table 2). All of the clones were found to have both the heavy and light chains linked to SEQ ID NO: 2 (SP#579) with one exception; Her.2.24 was found to have heavy chains with both SEQ ID NO: 1 (SP#552) and SEQ ID NO: 2 (SP#579).

TABLE 2

Trastuzumab titers and signal peptides in top clones

| Clone # | strain ID# | Signal peptide on light chain | Signal peptide on heavy chain | Titers (mg/L) |
|---|---|---|---|---|
| Her.1.2 | #5942 | 579 | 579 | 30 |
| Her.2.24 | #5950 | 579 | 552, 579 | 16 |

Example 3—Construction of Alg3 Deletion Cassettes

This example describes the construction of a linear fragment of DNA for the disruption of the alg3 gene. Three Alg3 genes identified as SG4EUKT579099 (SEQ ID NO: 3), SG4EUKT579102 (SEQ ID NO: 4), and SG4EUKT561246 (SEQ ID NO: 5) were found in the genome assembly of the wt *Aurantiochytrium* sp. All three sequences encode a 434 amino acid protein. SG4EUKT579099 and SG4EUKT579102 are identical at both the amino acid and nucleotide levels. SG4EUKT561246 has more than 99% identity to the other sequences at both the amino acid and nucleotide levels. This high level of identity allowed for the deletion of all three sequences with a single disruption cassette (alg3::nat) comprised of a selectable marker (nat) (which provides resistance to nourseothricin) flanked by 5' and 3' alg3 homology arms. The alg3::nat disruption cassette was generated by amplifying the 5' and 3' alg3 homology arms from a wild type strain genomic DNA, while the selectable marker (nat) was amplified from nat containing plasmid DNA.

Example 4—Deletion of Alg3

A trastuzumab-producing strain was transformed with the linear alg3::nat disruption cassette described in Example 3. Nourseothricin-resistant colonies were screened for the deletion of alg3 by quantitative PCR (qPCR). Four clones were identified that had Alg3 deleted and these clones were given strain IDs: #6667, #6668, #6669, and #6670.

Example 5—Antibody Production in 24 Well Plates

The alg3 deletion clones described in Example 4 were cultivated in 24 well plates for 22 hours and the trastuzumab levels in the supernatant were determined by ELISA. The results are shown in Table 3.

TABLE 3

Trastuzumab titers in small scale cultures of alg3 deleted clones.

| Strain ID | Trastuzumab titers (mg/L) |
|---|---|
| #6667 | 6.9 |
| #6668 | 7.5 |
| #6669 | 7.0 |
| #6670 | 9.8 |

Example 6—Fermentation of Alg3+ Strain and Alg3− Deletion Strain

Figure 3A:
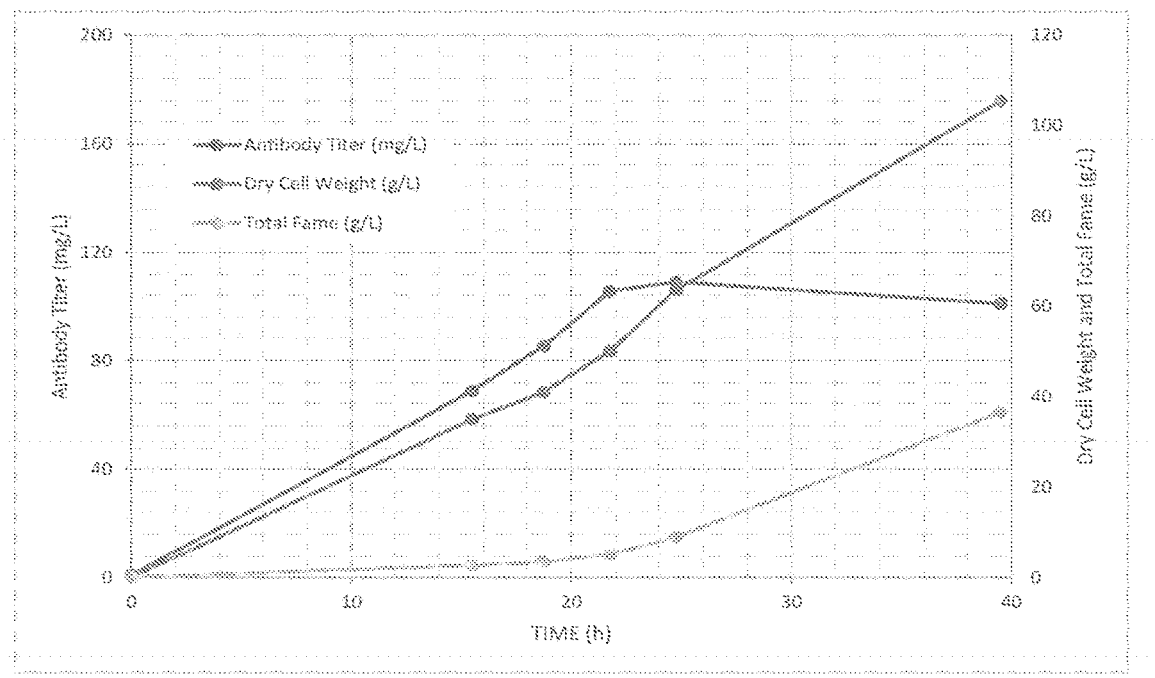
Figure 3B:
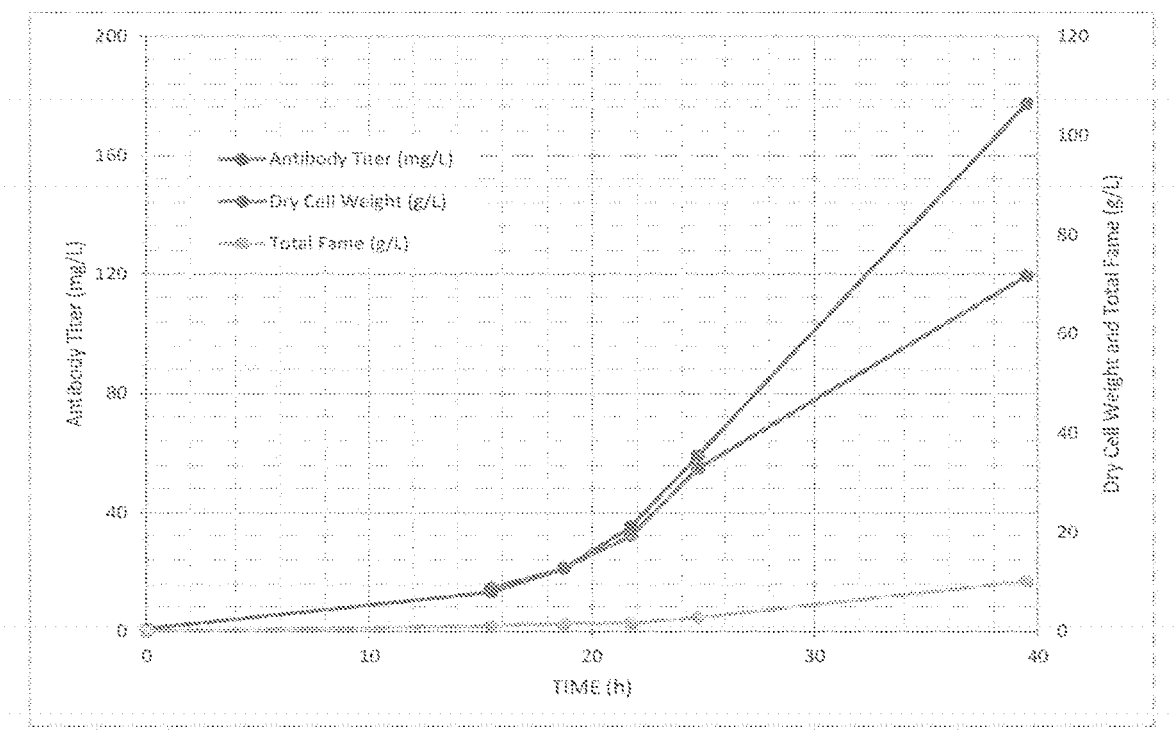

A 2-liter fermenter containing a medium (Table 4) comprised of yeast extract, peptone, salts, and glucose is inoculated with cells from a shake flask culture grown in a comparable medium. The production fermentation has a growth phase to increase cell density and produce the antibody. The production fermenter is operated until the culture reaches a biomass concentration between 50 to 100 g wet cell weight/L. A concentrated dextrose feed (Table 5) is started once the dextrose concentration reaches less than 5 g/L and henceforth, the dextrose concentration is kept below 1 g/L. The pH is maintained at 6.0 using 30% ammonium hydroxide or ammonia (pure gas). FIGS. 3*a* and 3*b* show the production of antibody (mg/L), biomass (g dry cell weight/L) and total FAME (g/L) produced by the fermentation that employed #5942 and #6670, respectively. This results are consistent with those from Example 3 as they clearly show that deletion of alg3 did not have a deleterious effect on antibody titers in 2 L fermentation.

TABLE 4

Production Medium Composition

| Medium Components | Concentration | Unit |
|---|---|---|
| Sodium Chloride (NaCl) | 0 to 24 | g/L |
| Calcium Chloride (CaCl$_2$) | 0 to 0.8 | g/L |
| Sodium Sulfate (Na$_2$SO$_4$) | 0 to 20 | g/L |
| Potassium Phosphate (KH$_2$PO$_4$) | 1 to 10 | g/L |
| Ammonium sulfate ((NH$_4$)$_2$SO$_4$) | 0 to 5 | g/L |
| Potassium Chloride (KCl) | 0 to 10 | g/L |
| Yeast Extract (Tastone 154) | 0 to 100 | g/L |
| Peptone BD | 0 to 100 | g/L |
| Magnesium Sulfate (MgSO$_4$•7H$_2$O) | 0 to 10 | g/L |
| Sodium EDTA-2H20 (Na$_2$EDTA•2H$_2$O) | 0 to 500 | mg/L |
| Boric Acid (H$_2$BO$_3$) | 0 to 500 | mg/L |
| Iron Chloride (FeCl$_2$•4H$_2$O) | 0 to 500 | mg/L |
| Cobalt Chloride (CoCl$_2$•6H$_2$O) | 0 to 500 | mg/L |
| Manganese Chloride (MnCl$_2$•4H$_2$O) | 0 to 1000 | µg/L |
| Zinc Chloride (ZnCl$_2$) | 0 to 1000 | µg/L |
| Nickel Sulfate (NiSO$_4$•6H$_2$O) | 0 to 1000 | µg/L |
| Copper Sulfate (CuSO$_4$•5H$_2$O) | 0 to 1000 | µg/L |
| Sodium Molybdenate (Na$_2$MoO$_4$•2H$_2$O) | 0 to 1000 | µg/L |
| Vitamin B12 | 0 to 1000 | µg/L |
| Biotin | 0 to 1000 | µg/L |
| Thiamine | 0 to 5000 | µg/L |

TABLE 5

Feed Composition for Production Fermentation

| Feed components | Concentration | Unit |
|---|---|---|
| Dextrose | 0 to 900 | g/L |
| Magnesium Sulfate (MgSO$_4$•7H$_2$O) | 0 to 50.0 | g/L |
| Yeast Extract (Tastone 154) | 0 to 100 | g/L |
| Peptone BD | 0 to 100 | g/L |
| Ammonium Sulfate ((NH$_4$)$_2$SO$_4$) | 0 to 50.0 | g/L |
| Sodium EDTA-2H$_2$O (Na$_2$EDTA•2H$_2$O) | 0 to 500 | mg/L |
| Iron Chloride (FeCl$_2$•4H$_2$O) | 0 to 500 | mg/L |
| Manganese Chloride (MnCl$_2$•4H$_2$O) | 0 to 500 | mg/L |
| Boric Acid (H$_2$BO$_3$) | 0 to 500 | mg/L |
| Sodium Molybdenate (Na$_2$MoO$_4$•2H$_2$O) | 0 to 1000 | µg/L |
| Zinc Chloride (ZnCl$_2$) | 0 to 1000 | µg/L |
| Cobalt Chloride (CoCl$_2$•6H$_2$O) | 0 to 1000 | µg/L |
| Copper Sulfate (CuSO$_4$•5H$_2$O) | 0 to 1000 | µg/L |
| Nickel Sulfate (NiSO$_4$•6H$_2$O) | 0 to 1000 | µg/L |
| Vitamin B$_{12}$ (Cyanocobalamin) | 0 to 1000 | µg/L |
| Biotin | 0 to 1000 | µg/L |
| Thiamine | 0 to 5000 | µg/L |

Example 7—Purification of Antibody

The antibodies from the supernatants produced via fermentation were purified using 3 steps: 1) flocculation to remove cells and other insoluble material by centrifugation; 2) buffer exchange using tangential flow filtration (TFF); 3) protein A capture and release chromatography.

Cell supernatants were mixed with 5 M NaCl and polyethyleneimine (PEI) to a final concentration of 0.2% w/v PEI and 0.3 M of additional NaCl. After mixing for 5 minutes at room temperature the solution was centrifuged at 5,250×g for 15 min at 4° C., followed by an additional centrifugation at 18,000 g for 20 min at 4° C. The supernatant was then subjected to TFF buffer exchange by passing 3 volumes of protein A binding buffer (20 mM sodium phosphate pH 7.0) through a 30,000 MWCO crossflow cassette. The recovered solution was filtered through a 0.45 µm cellulose acetate filter. The antibody was captured with a pre-equilibrated Protein A column. Non-specific bound proteins were removed from the resin by washing with 40 mL of biding buffer. The antibody was removed from the column using elution buffer (100 mM sodium citrate pH 3.0). Centrifugal columns were used to exchange buffers and formulate the antibody in phosphate buffered saline (PBS). Gel images for each of the purification steps are shown in FIG. 4. Antibody concentration was measured by the absorbance at 280 nm (extinction coefficient, e280=225,000 M$^{-1}$cm$^{-1}$); 34.4 mg and 53.6 mg of antibody were purified from the Alg3+ strain and Alg3− strain, respectively.

Example 8—Glycosylation Analyses

Purified antibodies produced by the Alg3+ and Alg3− strains were analyzed by release of glycans using PNGaseF and PNGaseA and analysis by MALDI TOF/TOF and ESI-MS. The analysis of all data give a complete picture of the number and abundance of all glycans present in each sample, as well as the structures in each sample.

The combined data from the previous analyses confirmed that N-linked glycosylation in both samples only occurred at the expected site, Asn327. There was no detectable O-glycosylation in either sample. A large number of high mannose glycans, some of which contained xylose and sulfated structures, were detected on antibody from Alg3+ strain; whereas far fewer N-linked glycans were observed on sample from Alg3− strain (FIGS. 4-5, 7 and 8). None of the N-linked glycans produced by Alg3− contain xylose. The majority of the N-linked glycans produced by Alg3− have a Man3 structure (FIG. 5 and FIG. 8).

These analyses show there is a drastic difference in the glycan profile after alg3 deletion. With respect to paucimannose N-glycans, based on the method of glycan release, there are between 0 and 3% in the Alg3+ strain profile, while there are between 89 and 90% in the Alg3− strain profile. Similarly, with respect to high mannose N-glycans, based on the method of glycan release, there are between 97% and 100% in the Alg3+ strain profile, while there are between 10% and 11% in the Alg3− strain profile. Thus, the deletion of alg3 resulted in a reduction (up to 90%) in high mannose N-glycans and a simultaneous increase (up to 3000%) in the production of paucimannose N-glycans.

Table 6 below shows differences between alg3+ and alg3− strains with respect to high mannose and paucimannose N-glycan profiles.

TABLE 6

| Strain | N-glyans | % N-linked glycans ||
|---|---|---|---|
| | | PNGaseF | PNGaseA |
| #5942 | High mannose | 97 | 100 |
| #5942 | Pauci-mannose | 3 | 0 |
| #6670 | High mannose | 10 | 11 |
| #6670 | Pauci-mannose | 90 | 89 |

Although the disclosure has been described with reference to the above examples, it will be understood that modifications and variations are encompassed within the spirit and scope of the disclosure. Accordingly, the disclosure is limited only by the following claims.

The invention claimed is:

1. A recombinant cell of the Class Labyrinthulomycetes comprising a genetic modification of a gene that encodes a mannosyl transferase, and further comprising a recombinant nucleic acid encoding a functional glycoprotein or glycopeptide, wherein the cell produces a heterologous glycoprotein or glycopeptide having an N-linked glycan profile that has at least 25% fewer high mannose structures than the N-linked glycan profile from a reference cell that does not comprise the genetic modification in the gene that encodes the mannosyl transferase.

2. The cell of claim 1 wherein the genetic modification is selected from a deletion, an insertion, a replacement, or a disruption.

3. The cell of claim 1 wherein the genetic modification is a deletion, and the mannosyl transferase is an alpha-1,3-mannosyl transferase.

4. The cell of claim 3 wherein the mannosyl transferase is of the class EC 2.4.1.258.

5. The cell of claim 1 wherein the glycoprotein is an antibody.

6. The cell of claim 5 wherein the heterologous glycoprotein is selected from the group consisting of: trastuzumab, eculizumab, natalizumab, cetuximab, omalizumab, usteinumab, panitumumab, and adalimumab, or a functional fragment of any of them.

7. The cell of claim 3 wherein the heterologous glycoprotein or glycopeptide has an N-linked glycan profile having at least 50% fewer high mannose N-linked glycans than the N-linked glycan profile from a Labyrinthulomycetes cell that does not comprise the mannosyl transferase deletion.

8. The cell of claim 1 wherein the glycoprotein or glycopeptide has an N-linked glycan profile having less than 50% high mannose structures.

9. The Labyrinthulomycetes cell of claim 3 selected from the group consisting of: *Aurantiochytrium, Schizochytrium*, and *Thraustochytrium*, further wherein the genetic modification is a deletion, and the mannosyl transferase is alg3.

10. The cell of claim 9 which is an *Aurantiochytrium* sp.

11. The cell of claim 1 wherein the glycoprotein or glycopeptide comprises at least 50% fewer high mannose structures.

12. The cell of claim 1 wherein the glycoprotein or glycopeptide comprises at least 25% more paucimannose structures versus the cell that does not comprise the mannosyl transferase genetic modification.

13. The cell of claim 1 wherein more than 50% of the N-linked glycans comprise a paucimannose structure.

14. The cell of claim 13 wherein the paucimannose structure comprises a Man3 structure.

15. A method of producing a glycoprotein or glycopeptide that comprises a simplified N-glycan profile comprising:
    a) performing a genetic modification in a gene that encodes a mannosyl transferase in a host cell of the Class Labyrinthulomycetes;
    b) cultivating the host cell;
    c) harvesting a glycoprotein or glycopeptide from the cell that has a simplified N-linked glycan profile wherein at least 50% of the N-linked glycans comprise a Man3 and/or Man4 glycan structure.

16. The method of claim 15 wherein the mannosyl transferase is an alpha-1,3-mannosyl transferase.

17. The method of claim 16 wherein the mannosyl transferase is of the class EC 2.4.1.258.

18. The method of claim 16 wherein the genetic modification is a deletion, and the glycoprotein is an antibody.

19. The cell of claim 18 wherein the glycoprotein antibody is selected from the group consisting of: trastuzumab, eculizumab, natalizumab, cetuximab, omalizumab, usteinumab, panitumumab, and adalimumab, or a functional fragment of any of them.

20. The method of claim 15 wherein the glycoprotein or glycopeptide comprises at least 50% fewer N-linked glycans versus a host cell that does not comprise the mannosyl transferase deletion.

21. The method of claim 15 wherein the N-linked glycan profile comprises less than 50% high mannose structures.

22. The method of claim 15 wherein the Labyrinthulomycete cell is selected from the group consisting of: *Aurantiochytrium, Schizochytrium*, and *Thraustochytrium*, further wherein the genetic modification is a deletion and the mannosyl transferase is alg3.

23. The method of claim 22 wherein the Labyrinthulomycete is an *Aurantiochytrium*.

24. The method of claim 15 wherein the glycoprotein or glycopeptide comprises at least 50% fewer high mannose structures.

25. The method of claim 15 wherein the glycoprotein or glycopeptide comprises at least 25% more paucimannose structures versus the cell that does not comprise the mannosyl transferase deletion.

26. The method of claim 15 wherein more than 50% of the N-linked glycans comprise a man3 glycan structure.

27. The method of claim 15 wherein the N-glycan structure comprises at least 70% Man3 and/or Man4 structures.

28. The recombinant cell of claim 3 wherein the gene that encodes a mannosyl transferase is alg3.

29. The method of claim 15 wherein the genetic modification is a deletion, and the gene that encodes a mannosyl transferase is alg3.

\* \* \* \* \*